US011752164B2

(12) United States Patent
Sundaram et al.

(10) Patent No.: US 11,752,164 B2
(45) Date of Patent: *Sep. 12, 2023

(54) BORTEZOMIB COMPOSITIONS

(71) Applicant: MAIA Pharmaceuticals, Inc., Princeton, NJ (US)

(72) Inventors: Srikanth Sundaram, Somerset, NJ (US); Daniel Charles Stewart, Queensbury, NY (US)

(73) Assignee: MAIA PHARMACEUTICALS, INC., Princeton, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 18/188,384

(22) Filed: Mar. 22, 2023

(65) Prior Publication Data
US 2023/0218647 A1   Jul. 13, 2023

Related U.S. Application Data

(63) Continuation of application No. 17/934,901, filed on Sep. 23, 2022, now Pat. No. 11,679,119.

(60) Provisional application No. 63/248,314, filed on Sep. 24, 2021.

(51) Int. Cl.

| | | |
|---|---|---|
| *A61K 31/69* | (2006.01) | |
| *A61K 9/08* | (2006.01) | |
| *A61K 47/12* | (2006.01) | |
| *A61K 47/20* | (2006.01) | |
| *A61K 47/26* | (2006.01) | |
| *A61P 35/00* | (2006.01) | |
| *A61K 47/02* | (2006.01) | |
| *A61K 9/00* | (2006.01) | |
| *A61K 31/198* | (2006.01) | |
| *A61K 31/4439* | (2006.01) | |
| *A61K 31/573* | (2006.01) | |
| *A61K 45/06* | (2006.01) | |
| *A61K 47/18* | (2017.01) | |
| *A61K 47/40* | (2006.01) | |

(52) U.S. Cl.
CPC .......... *A61K 31/69* (2013.01); *A61K 9/0019* (2013.01); *A61K 9/08* (2013.01); *A61K 31/198* (2013.01); *A61K 31/4439* (2013.01); *A61K 31/573* (2013.01); *A61K 45/06* (2013.01); *A61K 47/02* (2013.01); *A61K 47/12* (2013.01); *A61K 47/183* (2013.01); *A61K 47/20* (2013.01); *A61K 47/26* (2013.01); *A61K 47/40* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 6,699,835 B2 | 3/2004 | Plamondon et al. | |
| 6,713,446 B2 | 3/2004 | Gupta | |
| 6,958,319 B2 | 10/2005 | Gupta | |
| 8,263,578 B2 | 9/2012 | Soppimath et al. | |
| 11,672,813 B2* | 6/2023 | Sundaram ............ | A61K 31/198 514/64 |
| 11,679,119 B2* | 6/2023 | Sundaram ............ | A61K 31/69 424/401 |
| 2008/0187604 A1 | 8/2008 | Tomaselli et al. | |
| 2008/0200478 A1 | 8/2008 | Robinson | |
| 2017/0143622 A1 | 5/2017 | Shaik et al. | |
| 2017/0239335 A1 | 8/2017 | Sonavaria et al. | |
| 2018/0110822 A1 | 4/2018 | Chandrashekhar et al. | |
| 2022/0133757 A1* | 5/2022 | Yu ....................... | A61K 47/183 514/64 |

FOREIGN PATENT DOCUMENTS

| | | |
|---|---|---|
| CN | 106265536 A | 1/2017 |
| WO | 2016001905 A2 | 1/2016 |
| WO | 2016059590 A1 | 4/2016 |
| WO | 2017013208 A1 | 1/2017 |
| WO | 2017013209 A1 | 1/2017 |

OTHER PUBLICATIONS

Campbell (Can. J. Chem 57, 705 (1979) (Year: 1979).
Velcade prescribing information, 2019.
Dec. 5, 2022 Restriction Requirement in U.S. Appl. No. 17/934,873.
Jan. 5, 2023 Office Action in U.S. Appl. No. 17/934,889.
Invega Hafvera Prescribing Information, 2006.
ISR and Written Opinion issued in PCT/US22/44537 dated Feb. 8, 2023.
Jan. 5, 2023 Restriction Requirement in U.S. Appl. No. 17/934,884.
Office Action dated Jan. 12, 2023 in U.S. Appl. No. 17/934,873.
Office Action dated Jan. 27, 2023 in U.S. Appl. No. 17/934,884.
Velcade Package Insert, FDNMPI Finalized May 13, 2003.
Product Quality Review for NDA 205004, US Food and Drug Administration. Center for Drug Evaluation and Research, Bortezomib Injection, Approval Date: Nov. 6, 2017.

* cited by examiner

*Primary Examiner* — Melissa S Mercier
(74) *Attorney, Agent, or Firm* — Blank Rome LLP

(57) ABSTRACT

The present disclosure relates to ready-to-use liquid aqueous bortezomib compositions bortezomib and pharmaceutical excipients. Other aspects include methods of preparing such ready-to-use liquid aqueous bortezomib compositions, and methods of using such ready-to-use liquid bortezomib compositions in therapeutic applications.

12 Claims, No Drawings

BORTEZOMIB COMPOSITIONS

This application is a continuation of U.S. patent application Ser. No. 17/934,901, filed Sep. 23, 2022 which claims the benefit of U.S. Provisional Application No. 63/248,314, filed Sep. 24, 2021, the contents of which are hereby incorporated by reference in its entirety.

FIELD OF THE INVENTION

The disclosure relates to bortezomib compositions, methods of preparing such compositions, and methods of using such compositions in therapeutic applications.

BACKGROUND OF THE INVENTION

Boronic acids have found medical use as VELCADE® which has been approved for the treatment of patients with multiple myeloma, and for the treatment of patients with mantle cell lymphoma.

Bortezomib reversibly inhibits chymotrypsin-like activity of mammalian 26S proteasomes, a large protein complex which is responsible for degradation of ubiquitinated proteins. This pathway plays an essential role in managing the intracellular concentration of specific proteins, thereby maintaining homeostasis. Inhibition of the 26S proteasome would prevent targeted proteolysis, affecting multiple signaling cascades within a cell. This disruption of normal homeostatic mechanisms can lead to cell death. Bortezomib has been shown to be cytotoxic to a variety of cancer cell types in vitro. Further, bortezomib causes a delay in tumor growth in vivo in nonclinical tumor models, including multiple myeloma.

The currently marketed, lyophilized form of bortezomib (VELCADE®) contains a bortezomib ester and mannitol. VELCADE® is provided as a lyophilized formulation comprising the specific mannitol-boronic ester, which, when reconstituted, is present as the mannitol-boronic ester in equilibrium with its hydrolysis product, the monomeric boronic acid. The active pharmaceutical ingredient used in VECLADE can also exist in its cyclic anhydride form as a trimeric boroxine.

Bortezomib formulations have been marketed as injectable products which are distributed as lyophilized powders for reconstitution with aqueous 0.9% sodium chloride solution promptly before administration. The volume used to reconstitute the product will depend on the route of injection, whether subcutaneous (final concentration of bortezomib, 2.5 mg/mL) or intravenous (final concentration of bortezomib, 1 mg/mL). VELCADE® (and other similar lyophilized products) is labeled for use within 8 hours of its reconstitution, and for storage (in the original vial or in a syringe, under normal indoor lighting) at 25° C.

Bortezomib indeed has a history of being unstable, rapidly degrading in liquid formulations, and having generally poor solubility. Numerous attempts to develop a stable liquid formulation of bortezomib have been largely unsuccessful.

International Publication Nos. WO 2017/013208 and WO 2017/013209 disclose preparing an aqueous bortezomib solution by dissolving bortezomib in water.

U.S. Pat. No. 8,263,578 describe bortezomib formulations which have propylene glycol as a predominant component and are substantially non-aqueous.

U.S. Patent Publication No. 2018/0110822 disclose bortezomib formulations containing DOTA and monothioglycerol.

There is a continuing need for improved formulations of bortezomib, in particular, aqueous liquid ready-to-use formulations with improved stability that are suitable for direct parenteral administration.

SUMMARY OF THE INVENTION

In some aspects, the disclosure provides liquid, ready-to-use, aqueous compositions, comprising bortezomib, water, a non-aqueous solvent and one or more pharmaceutically acceptable excipients, wherein at least about 50% by volume of the liquid composition, based on the total volume of the liquid composition, is aqueous.

In other aspects, the disclosure provides intravenous, ready-to-use dosage forms, comprising bortezomib, mannitol, dimethyl sulfoxide, sodium acetate, and water.

In other aspects, the disclosure provides intravenous, ready-to-use dosage forms comprising bortezomib, mannitol, dimethyl sulfoxide, sodium acetate, water and, optionally, hydrochloric acid, sodium hydroxide, or a combination thereof.

In other aspects, the disclosure provides an intravenous, ready-to-use dosage form comprising about 1 mg/mL bortezomib, about 10 mg/mL mannitol, about 20 mg/mL dimethyl sulfoxide, about 0.82 mg/mL sodium acetate, water and, optionally, hydrochloric acid, sodium hydroxide, or a combination thereof. In one embodiment, the dosage form is 3.5 mL and is optionally stored in a 5 mL vial. The pH of the dosage form may be from about 5 to about 6.

In other aspects, the disclosure provides an intravenous, ready-to-use dosage forms comprising about 2.5 mg/mL bortezomib, about 25 mg/mL mannitol, about 22 mg/mL dimethyl sulfoxide, about 0.82 mg/mL sodium acetate, water and, optionally, hydrochloric acid, sodium hydroxide, or a combination thereof. In one embodiment, the dosage form is 1.4 mL and is optionally stored in a 2 mL vial. The pH of the dosage form may be from about 5 to about 6.

In further aspects, the disclosure provides subcutaneous, ready-to-use dosage forms, comprising bortezomib, mannitol, dimethyl sulfoxide, sodium acetate, and water.

In other aspects, the disclosure provides subcutaneous, ready-to-use dosage forms comprising bortezomib, mannitol, dimethyl sulfoxide, sodium acetate, water and, optionally, hydrochloric acid, sodium hydroxide, or a combination thereof.

In other aspects, the disclosure provides a subcutaneous, ready-to-use dosage forms, comprising about 1 mg/mL bortezomib, about 10 mg/mL mannitol, about 20 mg/mL dimethyl sulfoxide, about 0.82 mg/mL sodium acetate, water and, optionally, hydrochloric acid, sodium hydroxide, or a combination thereof. In one embodiment, the dosage form is 3.5 mL and is optionally stored in a 5 mL vial. The pH of the dosage form may be from about 5 to about 6.

In other aspects, the disclosure provides a subcutaneous, ready-to-use dosage forms, comprising about 2.5 mg/mL bortezomib, about 25 mg/mL mannitol, about 22 mg/mL dimethyl sulfoxide, about 0.82 mg/mL sodium acetate, water and, optionally, hydrochloric acid, sodium hydroxide, or a combination thereof. In one embodiment, the dosage form is 1.4 mL and is optionally stored in a 2 mL vial. The pH of the dosage form may be from about 5 to about 6.

In yet other aspects, the disclosure provides processes of preparing a liquid, ready-to-use aqueous composition comprising bortezomib.

In still further aspects, the disclosure provides methods of using the liquid, ready-to-use, aqueous compositions, intravenous dosage forms, or the subcutaneous forms described herein, comprising administering the same to a patient in need of administration.

In other aspects, the disclosure provides methods of treating a cancer in a patient in need of treatment, comprising administering the liquid, ready-to-use, aqueous compositions, the intravenous dosage forms, or the subcutaneous forms to the patient.

In other aspects, the disclosure provides methods of administering bortezomib by intravenously administering the liquid, ready-to-use, aqueous composition described herein.

Other aspects and embodiments of the invention will be readily apparent from the following detailed description of the invention.

DETAILED DESCRIPTION OF THE INVENTION

The liquid, aqueous ready-to-use bortezomib compositions disclosed herein are storage stable compositions comprising bortezomib (or a pharmaceutically acceptable salt thereof), water, a non-aqueous solvent and one or more pharmaceutically acceptable excipients. In particular embodiments, these liquid compositions are formulated and prepared using a lyophilizer-based process for controlling the headspace oxygen content in the vial.

The liquid, ready-to-use, aqueous composition described herein are physically stable with solubility of greater than 1 mg/mL for intravenous administration, or greater than 2.5 mg/mL for subcutaneous administration. The liquid, ready-to-use, aqueous compositions described herein provide a pH similar to a commercially approved bortezomib product, VELCADE, which has a reported pH range of 4 to 7 after reconstitution. The liquid, ready-to-use, aqueous composition also provide very low levels of non-aqueous solvents that are compatible with parenteral administration, at or below the permissible daily exposure (PDE) levels. In certain aspects, such non-aqueous solvents may be considered "residual solvents" in pharmaceutical drug products that are safe for direct intravenous or subcutaneous administration without reconstitution and/or dilution. See, e.g., ICH Harmonized Guideline. Impurities: Guideline for Residual Solvents Q3C(R8). International Council for Harmonization of Technical Requirements for Pharmaceuticals for Human Use. 2021, which is incorporated by reference herein.

A portion of the bortezomib in the mannitol-containing liquid compositions described herein may form an ester with mannitol. The mannitol-containing liquid compositions described herein may contain the mannitol ester of bortezomib in equilibrium with its hydrolysis product, i.e., bortezomib.

As used herein, the term "residual solvents" refer to solvents used in pharmaceutical products that are not completely removed by practical manufacturing techniques. Thus, such residual solvents are safe to administer at acceptable levels.

The liquid, ready-to-use, aqueous composition described herein further provide good stability, such that bortezomib is maintained at least 90% as measured by a high-performance liquid chromatographic assay, when stored at temperatures of from about 0° C. to about 40° C., under relative humidity conditions of about 65% to about 75%, for at least a month. In some aspects, the stability of bortezomib is maintained at least about 91%, about 92%, about 93%, about 94%, about 95%, about 96%, about 97%, about 98%, about 99%, or 100%. In certain aspects, the relative humidity conditions are about 65% to about 70% or about 70% to about 75%, about 65%, about 70%, or about 76%. In other aspects, the liquid, ready-to-use, aqueous composition are stored at temperatures of about 0° C., about 10° C., about 20° C., about 30° C., or about 40°, 0 to about 30° C., about 0 to about 20° C., about 0 to about 10° C., 10 to about 40° C., about 10 to about 30° C., about 10 to about 2° C. 0, about 20 to about 40° C., about 20 to about 30° C., or about 30 to about 40° C. In yet other aspects, the liquid, ready-to-use, aqueous composition are storage stable for at least two months, or for at least three months, or for at least six months, or for at least 9 months or for at least 12 months, or at least 18 months, or at least 24 months.

The present disclosure is generally directed towards the liquid, ready-to-use, aqueous composition and methods of preparing and using liquid aqueous ready-to-use compositions containing therapeutically effective concentrations of bortezomib, where the compositions provide storage stability for bortezomib. These liquid, ready-to-use, aqueous composition described herein are primarily aqueous, having at least about 50%, at least about 60%, at least about 75%, at least about 80%, at least about 90%, at least about 95%, or at least about 98% water content. These liquid, ready-to-use, aqueous composition are superior to bortezomib formulations in the art, which are not primarily aqueous in nature, and are substantially non-aqueous (i.e., contain at least 50% or more of non-aqueous solvent).

Definitions

In the disclosure, the singular forms "a", "an" and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about" or "approximately" it will be understood that the particular value forms another embodiment. In general, use of the term "about" or "approximately" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about" or "approximately." In other cases, the gradations used in a series of values may be used to determine the intended range available to the term "about" or "approximately" for each value. Where present, all ranges are inclusive and combinable. That is, references to values stated in ranges include every value within that range.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

It is to be appreciated that certain features of the invention which are, for clarity, described herein in the context of separate embodiments, may also be provided in combination in a single embodiment. That is, unless obviously incompatible or excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. It is further noted that the claims may be drafted to exclude an optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

"Pharmaceutically acceptable salt" as used herein refers to salts of bortezomib that are pharmaceutically acceptable and possess the activity of the neutral bortezomib. The salts are non-toxic and include inorganic acid, organic acid, or base addition salts. In some embodiments, the salts are inorganic acid salts. In other embodiments, the salts are formed with inorganic acids including, without limitation, hydrochloric acid, hydrobromic acid, sulfuric acid, nitric acid, or phosphoric acid. In further embodiments, the salts are formed using organic acids. In still other embodiments, the salts are formed with organic acids including, without limitation, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxy ethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, or muconic acid. The pharmaceutically acceptable salts may also be formed by replacing an acidic proton in bortezomib with metal ion (alkali, alkaline earth, aluminum) or coordinates with an organic base (ethanolamine, diethanolamine, triethanolamine, N-methylglucamine).

The terms "subject" and "patient" are used interchangeably and include, without limitation, mammals. In some embodiments, the patient or subject is a human. In other embodiments, the patient or subject is a veterinary or farm animal, a domestic animal or pet, or animal used for clinical research.

"Treating" or variations thereof refers ameliorating or reducing the development of a disease or disorder, i.e., delaying the onset of the disease. In other embodiments, "treating" refers to ameliorating or reducing at least one physical parameter of the disease or disorder.

As used herein, the "one or more additional therapeutic agents" employed in the methods described herein include those agents that are known to be useful for treating cancer, i.e., having a therapeutic effect on, alleviating one or more symptoms of, altering the progression of, eradicating, reducing the size of, slowing or inhibiting the growth of, delaying or minimizing one or more symptoms associated with, reducing the malignancy of, or inducing stasis of the cancer, or alleviating or minimizing one or more side effects associated with another therapy applied or administered to treat the cancer. In some aspects, the additional therapeutic agent is lenalidomide, dexamethasone, melphalan, or prednisone, or a combination thereof. In other aspects, the additional therapeutic agent is lenalidomide. In further aspects, the additional therapeutic agent is dexamethasone. In yet other aspects, the additional therapeutic agent is melphalan. In still further aspects, the additional therapeutic agent is prednisone.

As used herein, the term "formulation" or "composition" refers to bortezomib forms suited to the administration of the compounds to subjects.

The term "ready-to-use" refers to the ability of one skilled in the art to dispense one or more of a composition, formulation, or dosage unit described herein with minimal if any effort or preparation. In some aspects, a ready-to-use product is prepackaged. In other aspects, ready-to-use refers to an injectable product described herein containing bortezomib in solution at the required concentration and volume in a container, e.g., vial (e.g., a glass vial). In one embodiment, the volume of the container is 2 mL. In another embodiment, the volume of the container is 5 mL. In further aspects, the injectable product may be transferred to a final container (syringe, infusion bag, or elastomeric device) for administration to the patient. See, e.g., "ISMP Safe Practice Guidelines for Adult IV Push Medication," Institute for Safe Medication Practices ISMP), 2015, which is incorporated herein by reference, which describes options for transferring the injectable product to a means for administering the bortezomib solution. Advantageously, the bortezomib liquid, ready-to-use, aqueous compositions have not been reconstituted from a lyophilized powder and/or diluted from a concentrate at any point.

The term "headspace" refers to the volume of a container that is occupied by gas and not occupied by a liquid. The amount of headspace that is required may be determined by one skilled in the art.

As used herein, the term "pharmaceutical grade" refers to a compound that has been filed with the FDA as a Drug Master File (DMF). In certain aspects, "pharmaceutical grade" refers to bortezomib that has been filed with the FDA as a Drug Master File (DMF).

The term "bioequivalent" means the absence of a significant difference in the rate and extent to which the active ingredient or active moiety in pharmaceutical equivalents or pharmaceutical alternatives becomes available at the site of drug action when administered at the same molar dose under similar conditions in an appropriately designed study. Two products are considered bioequivalent if the 90% confidence interval of the $C_{max}$, area under curve (AUC), or optionally, $T_{max}$ is within the range of 80.00% to 125.00%.

Bortezomib Compositions

The aqueous liquid, aqueous ready-to-use bortezomib compositions described herein comprise a pharmaceutically acceptable amount of the active ingredient, bortezomib (or a salt thereof), a non-aqueous solvent, and one or more pharmaceutically acceptable excipient. These liquid, ready-to-use, aqueous compositions are at least about 50% aqueous. In some embodiments, the liquid, ready-to-use, aqueous composition is at least about 60% aqueous, at least about 65% aqueous, at least about 70% aqueous, at least about 75% aqueous, at least about 80% aqueous, at least about 85% aqueous, at least about 90%, at least about 95%, or at least about 98% aqueous. A portion of the liquid, ready-to-use, aqueous compositions described herein can be non-aqueous, as detailed below.

Advantageously, the liquid, ready-to-use, aqueous compositions described herein do not need to be reconstituted, lyophilized, or diluted from a concentrate. Products that are readily available for patient administration or eliminate preparation steps, like the liquid, ready-to-use, aqueous compositions and products described herein, are advantageous as they lead to more efficient use of hospital resources and fewer mixing mistakes and dosing errors. See, e.g., the "ASHP guidelines on preventing medication errors in hospitals." Am. J. Hosp. Pharm. 1993; 50:305-14 and "Pathways for Medication Safety: Looking Collectively at Risk. American Hospital Association, Health Research & Educational Trust and the Institute for Safe Medication Practices." 2002, both of which are incorporated by reference herein. Additionally, bortezomib is listed in the NIOSH list of antineoplastic and other hazardous drugs in healthcare settings as a Group 1 Hazardous Drug (HD). See, e.g., "NIOSH list of antineoplastic and other hazardous drugs in healthcare settings," 2016. U.S. Department of Health and Human Services, DHHS (NIOSH) Publication Number 2016-161, which is incorporated by reference. Constituting or reconstituting powdered or lyophilized HDs may result in potential exposure and recommends that such sterile HDs be prepared in special containment areas that mitigate this risk. However, a ready to use injection that does not require reconstitution, requiring less specialized containment strategies. See, e.g., United States Pharmacopeia. USP 800 FAQs. USP, 2020, pages 1-20, which is incorporated by reference herein. The ready-to-use, aqueous compositions described herein can be administered to a patient without further preparation, dilution, reconstitution, dispensing, sterilization, transfer, handling or compounding before parenteral administration (such as intravenous administration).

In one embodiment, the liquid, ready-to-use, aqueous compositions described herein is bioequivalent to VELCADE (3.5 mg/vial) (New Drug Application No. 21602). According to its prescribing information, VELCADE is administered intravenously at a concentration of 1 mg/mL or subcutaneously at a concentration of 2.5 mg/mL. In one embodiment, the liquid, ready-to-use, aqueous composition described herein (such as the 1 mg/mL or 2.5 mg/mL composition) is bioequivalent to VELCADE when administered intravenously at 1 mg/mL.

Bortezomib

The liquid, ready-to-use, aqueous compositions according to one aspect of the present disclosure may be prepared by the methods described herein, or by any method suitable to produce the liquid, ready-to-use, aqueous compositions. For example, the liquid, ready-to-use, aqueous composition includes bortezomib. Bortezomib is a chiral molecule with two chiral centers, and is the (S,R) stereoisomer. The chemical name of bortezomib, the monomeric boronic acid, is [(1R)-3-methyl-1-[[(2S)-1-oxo-3-phenyl-2-[(pyrazinylcarbonyl)amino]propyl]amino]butyl] boronic acid, and it has the following structure:

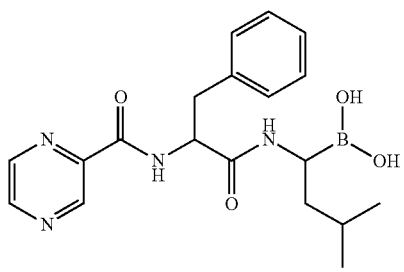

In certain embodiments, bortezomib has the following structure:

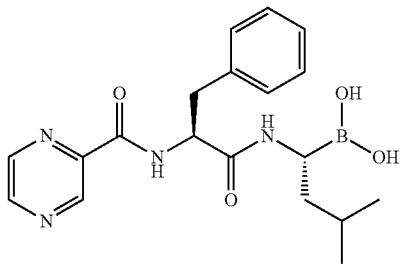 [SMILES: CC(C)C[C@H](NC(=O)[C@H](Cc1ccccc1)NC(=O)c1cnccn1)B(O)O]

Bortezomib is available as VELCADE® (Millennium Pharmaceuticals, Inc.) and in lyophilized forms marketed as Bortezomib for Injection by Fresenius Kabi (boric acid formulation and Dr. Reddy's Laboratories (citric acid formulation). In some aspects, the term bortezomib also includes pharmaceutically acceptable salts thereof. In other aspects, the term bortezomib further includes derivatives such as ester derivatives. See, e.g., the bortezomib ester derivatives described in U.S. Pat. Nos. 6,958,319; 6,699,835 and 6,713,446, which are incorporated herein by reference.

The term bortezomib also includes hydrates and cyclic anhydrides thereof, such as a trimeric boroxine. In some aspects, the term bortezomib refers to the bortezomib trimer, i.e., the trimeric boroxine compound having the following structure:

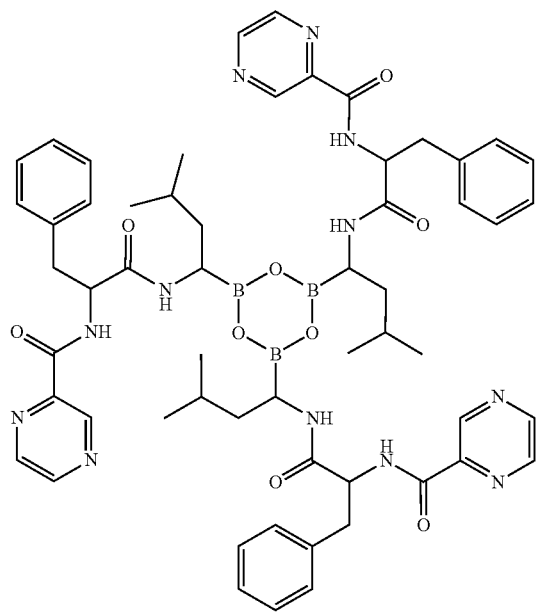 [SMILES: CC(C)CC(NC(=O)C(Cc1ccccc1)NC(=O)c1cnccn1)B1OB(C(CC(C)C)NC(=O)C(Cc2ccccc2)NC(=O)c2cnccn2)OB(C(CC(C)C)NC(=O)C(Cc2ccccc2)NC(=O)c2cnccn2)O1]

In certain embodiments, the bortezomib trimer has the following structure:

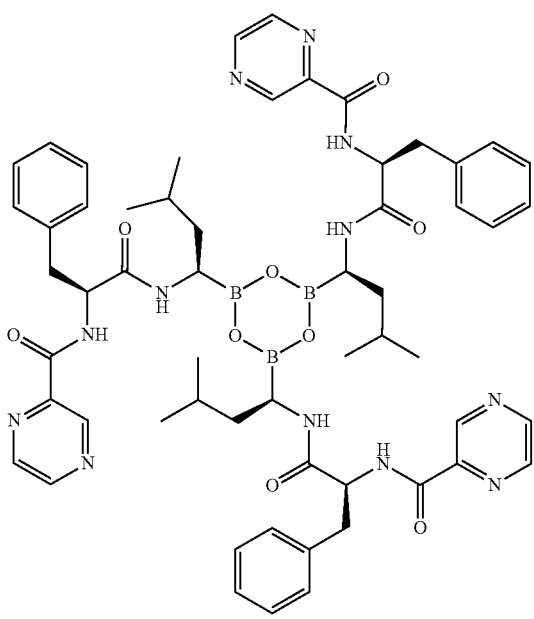 [SMILES: CC(C)C[C@H](NC(=O)[C@H](Cc1ccccc1)NC(=O)c1cnccn1)B1OB([C@H](CC(C)C)NC(=O)[C@H](Cc2ccccc2)NC(=O)c2cnccn2)OB([C@H](CC(C)C)NC(=O)[C@H](Cc2ccccc2)NC(=O)c2cnccn2)O1]

In other aspects, the term bortezomib refers to bortezomib monohydrate, which has the following structure:

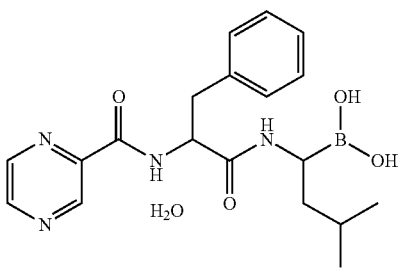

In certain embodiments, bortezomib has the following structure:

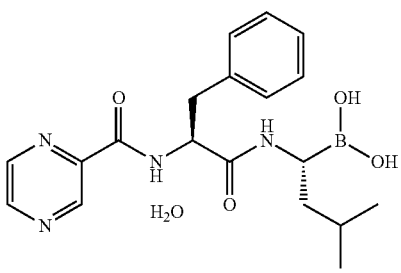

The liquid, ready-to-use, aqueous composition may contain any concentration of bortezomib that is necessary for use herein and as determined by one skilled in the art. In certain embodiments, the liquid, ready-to-use, aqueous composition contains about 0.5 to about 5 mg/mL of bortezomib. Such concentrations are based on the free base of bortezomib any may be adjusted by one skilled in the art depending on the form of bortezomib utilized. In other embodiments, the liquid, ready-to-use, aqueous composition contains about 0.5, about 1, about 1.5, about 2, about 2.5, about 3, about 3.5, about 4, or about 4.5 mg/mL of bortezomib. In further embodiments, the liquid, ready-to-use, aqueous composition contains about 0.5 to about 4.5, about 0.5 to about 4, about 0.5 to about 3.5, about 0.5 to about 3, about 0.5 to about 2.5, about 0.5 to about 2, about 0.5 to about 1.5, about 0.5 to about 1, about 1 to about 5, about 1 to about 4.5, about 1 to about 4, about 1 to about 3.5, about 1 to about 3, about 1 to about 2.5, about 1 to about 2, about 1 to about 1.5, about 1.5 to about 5, about 1.5 to about 4.5, about 1.5 to about 4, ab out 1.5 to about 3.5, about 1.5 to about 3, about 1.5 to about 2.5, about 1.5 to about 2, about 2 to about 5, about 2 to about 4.5, about 2 to about 4, about 2 to about 3.5, about 2 to about 3, about 2 to about 2.5, about 2.5 to about 5, about 2.5 to about 4.5, about 2.5 to about 4, about 2.5 to about 3.5, about 2.5 to about 3, about 3 to about 5, about 3 to about 4.5, about 3 to about 4, about 3 to about 3.5, about 3.5 to about 5, about 3.5 to about 4.5, about 3.5 to about 4, about 4 to about 5, about 4 to about 4.5, or about 4.5 to about 5 mg/mL of bortezomib. In yet other embodiments, liquid, ready-to-use, aqueous composition contains about 0.5 to about 1.5 mg/mL of bortezomib. In further embodiments, the liquid, ready-to-use, aqueous composition contains about 0.75 to about 1.25 mg/mL of bortezomib. In yet other embodiments, the liquid, ready-to-use, aqueous composition contains about 1 mg/mL of bortezomib. In still further embodiments, the liquid, ready-to-use, aqueous composition contains about 2 to about 3 mg/mL of bortezomib. In other embodiments, the liquid, ready-to-use, aqueous composition contains about 2.25 to about 2.75 mg/mL of bortezomib. In further embodiments, the liquid, ready-to-use, aqueous composition contains about 2.5 mg/mL of bortezomib.

The liquid, ready-to-use, aqueous composition may any amount of bortezomib that is necessary for use herein and as determined by one skilled in the art. In certain embodiments, the liquid, ready-to-use, aqueous composition contains about 0.5 to about 10 mg of bortezomib. Such amounts are based on the free base of bortezomib any may be adjusted by one skilled in the art depending on the form of bortezomib utilized. In other embodiments, the liquid, ready-to-use, aqueous composition contains about 0.5, about 1, about 2, about 3, about 4, about 5, about 6, about 7, about 8, about 9, or about 10 mg of bortezomib. In further embodiments, the liquid, ready-to-use, aqueous composition contains about 1 to about 10, about 1 to about 9, about 1 to about 8, about 1 to about 7, about 1 to about 6, about 1 to about 5, about 1 to about 4, about 1 to about 3, about 1 to about 2, about 2 to about 10, about 2 to about 9, about 2 to about 8, about 2 to about 7, about 2 to about 6, about 2 to about 5, about 2 to about 4, about 2 to about 3, about 3 to about 10, about 3 to about 9, about 3 to about 8, about 3 to about 7, about 3 to about 6, about 3 to about 5, about 3 to about 4, about 4 to about 10, about 4 to about 9, about 4 to about 8, about 4 to about 7, about 4 to about 6, about 4 to about 5, about 5 to about 10, about 5 to about 9, about 5 to about 8, about 5 to about 7, about 5 to about 6, about 6 to about 10, about 6 to about 9, about 6 to about 8, about 6 to about 7, about 7 to about 10, about 7 to about 9, about 7 to about 8, about 8 to about 10, about 8 to about 9, or about 9 to about 10 mg of bortezomib.

Non-Aqueous Solvent

Non-aqueous solvents are included in the liquid, ready-to-use, aqueous compositions and can act to facilitate the introduction of the active ingredient into the aqueous solution. The non-aqueous solvent may be selected based on the bortezomib solubility in the same. In some embodiments, bortezomib may be very soluble (defined as less than 1 part solvent required for 1 part of bortezomib) or freely soluble (defined as from 1 to 10 parts of solvent required for 1 part of bortezomib) in the non-aqueous solvent. In some embodiments, bortezomib has a solubility of greater than about 50 mg/mL in the non-aqueous solvent. In other embodiments, bortezomib has a solubility of greater than about 50, about 60, about 70, about 80, about 90, about 95, or about 99 mg/mL in the non-aqueous solvent. In further embodiments, bortezomib has a solubility of about 50 to about 90, about 50 to about 80, about 50 to about 70, about 50 to about 60, about 60 to about 90, about 60 to about 80, about 60 to about 70, bout 70 to about 90, about 70 to about 80, or about 80 to about 90 mg/mL in the non-aqueous solvent.

In some aspects, the non-aqueous solvent functions as a solubilizer, a stabilizer, a tonicity adjustor, or a combination thereof. In particular embodiments, the non-aqueous solvent includes pharmaceutically acceptable polar aprotic or protic materials. In some aspects, the non-aqueous solvent is a polar aprotic solvent. In other aspects, the non-aqueous solvent is a polar protic solvent. In other embodiments, the non-aqueous solvent is polyethylene glycol, N,N-dimethylacetamide, N-methyl pyrrolidone, glycerol, glycerol, propylene glycol, ethanol, t-butyl alcohol, benzyl alcohol, benzyl benzoate, or dimethyl sulfoxide. In further embodiments, the non-aqueous solvent is polyethylene glycol. In yet other embodiments, the non-aqueous solvent is N,N-dimethylacetamide. In still further embodiments, the non-aqueous solvent is N-methyl pyrrolidone. In other embodiments, embodiments, the non-aqueous solvent is glycerol. In further embodiments, the non-aqueous solvent is propylene glycol. In still other embodiments, the non-aqueous solvent is ethanol. In yet further embodiments, the non-aqueous solvent is t-butyl alcohol. In other embodiments, the non-aqueous solvent is benzyl alcohol. In further embodiments, the non-aqueous solvent is benzyl benzoate. In still other embodiments, the non-aqueous solvent is dimethyl sulfoxide.

In one embodiment of any of the liquid, ready-to-use, aqueous compositions described herein, the composition contains dimethyl sulfoxide (e.g., about 20 mg/mL or about 22 mg/mL dimethyl sulfoxide) as the non-aqueous solvent.

In one embodiment of any of the liquid, ready-to-use, aqueous compositions described herein, the composition does not contain a glycol (e.g., propylene glycol), or a $C_1$-$C_6$ alcohol (e.g., ethanol or isopropanol) as the non-aqueous solvent. In another embodiment, the compositions described herein does not contain a chelating agent, such as DOTA (1,4,7,10-tetraazacyclododecane-1,4,7,10-tetraacetic acid), DTPA (diethylene triaminepentaacetic acid), EDTA (ethylenediaminetetraacetic acid), ODDA (1,4,10,13-tetraoxa-7,16-diazacyclooctadecane-7), TTTA (1,7,13-triaza-4,10,16-trioxacyclooctadecane-N,N',N"-triacetate), DOTRP (tetraethyleneglycol-1,5,9-triazacyclododecane-N,N',N"-tris(methylene phosphonic acid), and EGTA (ethylene glycol-bis(β-aminoethyl ether)-tetraacetic acid). In yet another embodiment, the compositions described herein does not contain a sugar or amino acid (such as L-arginine). In yet another embodiment, the compositions described herein does not contain an anti-oxidant, such as monothioglycerol, ascorbic acid, sodium bisulfite, sodium metabisulfite, L-cysteine, thioglycolic acid, citric acid, tartaric acid, phosphoric acid, gluconic acid, and thiodipropionic acid. In yet another embodiment, the compositions described herein does not contain a glycol, a $C_1$-$C_6$ alcohol, a chelating agent (such as DOTA), a sugar, an amino acid (such as L-arginine), and an anti-oxidant (such as monothioglycerol).

In the liquid, ready-to-use, aqueous composition, such non-aqueous solvents can be present in amounts of for example, from about 0.1% to about 30% by volume or weight, based on the total volume or weight of the liquid, ready-to-use, aqueous composition. In some embodiments, the liquid, ready-to-use, aqueous composition comprises about 0.3% to about 15%, about 0.3 to about 10%, about 1% to about 5% by volume or weight, or about 2% to about 4% by volume or weight, based on the total volume or weight of the liquid, ready-to-use, aqueous composition. In other embodiments, the liquid, ready-to-use, aqueous composition contains about 0.1%, about 0.5%, about 1%, about 5%, about 10%, about 15%, about 20%, about 25%, or about 30% by volume or weight of the non-aqueous solvent, based on the volume or weight of the liquid, ready-to-use, aqueous composition.

Pharmaceutically Acceptable Excipients

The liquid, ready-to-use, aqueous compositions described herein contain at least one pharmaceutically acceptable excipient. The pharmaceutically acceptable excipients are selected based on the mode of administration and may include inert and/or active components. The pharmaceutically acceptable excipient may be selected based on the bortezomib solubility in the same. In some embodiments, bortezomib is very soluble or freely soluble in the selected pharmaceutically acceptable excipient. In some embodiments, bortezomib has a solubility of greater than about 50 mg/mL in the pharmaceutically acceptable excipient. In other embodiments, bortezomib has a solubility of greater than about 50, about 60, about 70, about 80, about 90, about 95, or about 99 mg/mL in the pharmaceutically acceptable excipient. In further embodiments, bortezomib has a solubility of about 50 to about 90, about 50 to about 80, about 50 to about 70, about 50 to about 60, about 60 to about 90, about 60 to about 80, about 60 to about 70, bout 70 to about 90, about 70 to about 80, or about 80 to about 90 mg/mL in the pharmaceutically acceptable excipient. In some embodiments, the pharmaceutically acceptable excipient is sterile, non-toxic, and/or biologically suitable for administration to a subject, i.e., buffered to an appropriate pH and isotonicity. In other embodiments, the pharmaceutically acceptable excipients include diluents (such as inert), carrier, adjuvant, fillers, disintegrants, binders, lubricants, sweeteners, flavors, colors, or preservatives. In some aspects, the pharmaceutically acceptable excipient is a solubilizer and/or stabilizer. Bortezomib is poorly soluble in water. Further its solubility is dependent on the chemical and physical characteristics of the drug substance such as water content, its crystallinity or amorphism, and its polymorphism.

In certain embodiments, the pharmaceutically acceptable excipient is a solubilizer. Solubilizers may include sugars, including monosaccharides, disaccharides, or sugar alcohols. Non-limiting examples of sugars include, without limitation, glucose, sucrose, fructose, or trehalose. Non-limiting examples of sugar alcohols include, without limitation, mannitol, sorbitol, and xylitol. In some embodiments, the solubilizer may also function as a stabilizer and/or tonicity adjustor.

In other embodiments, the pharmaceutically acceptable excipient is a stabilizer.

Stabilizers may be used advantageously in the liquid ready-to-use aqueous bortezomib compositions described herein. In certain aspects, at least one of the pharmaceutically acceptable excipient is a stabilizer. In some embodiments, the stabilizers may include stabilize bortezomib from deboronation, oxidation, and/or hydrolysis. In some aspects, the stabilizer is a pharmaceutically acceptable inorganic chloride, e.g., potassium chloride, sodium chloride, magnesium chloride or calcium chloride. In certain aspects, the stabilizer is 0.9% NaCl. In other aspects, the stabilizer is a saccharide such as mannitol (including D-mannitol), sorbitol, lactose, trehalose, raffinose, dextrose, maltose, galactose, sucrose, or polysucrose. In further aspects, the stabilizer is mannitol. In yet other aspects, the stabilizer is D-mannitol. In still further aspects, the stabilizer is 5% D-mannitol. In other aspects, the stabilizer is a polymer such as polyethylene glycol, polygalacturonic acid, galacturonic acid, polyvinylpyrrolidine (PVP), for example, PEG 300, PEG 400, PEG 3350, PEG 6000, or PEG 8000. In further aspects, the stabilizer is an amino acid such as lysine, arginine, glycine, methionine, or other amino acids. In still other aspects, the stabilizer is a cyclodextrin such as dextran, Ficoll, and polyvinylpyrrolidone, or other similar excipients and combinations of these agents.

In one embodiment of any of the liquid, ready-to-use aqueous formulations described herein, the composition does not contain an inorganic chloride (such as potassium chloride, sodium chloride, magnesium chloride or calcium chloride).

In yet further aspects, the stabilizer is an anti-oxidant, reducing agent, or chelating agents. In some aspects, the stabilizer is an antioxidant. In other aspects, the stabilizer is a reducing agent. In further aspects, the stabilizer is a tonicity adjuster. A wide variety of antioxidants or reducing agents can be used as stabilizers, including but not limited to, acetylcysteine, cysteine, methionine, ascorbic acid, benzyl alcohol, citric acid, pentetic acid or diethylenetriamine pentaacetic acid (DTPA), propyl gallate, methylparaben, sulfoxylate, propylparaben, edetic acid or ethylenediaminetetraacetic acid (EDTA), disodium EDTA dihydrate, dithiothreitol, glutathione, monothioglycerol, potassium metabisulfite, sodium formaldehyde sulfoxylate, sodium sulfite, sodium succinate, sodium metabisulfite, stannous chloride, thioacetic acid, thiodiglycerol, thioethanolamine, thioglycolic acid, 2-aminoethanethiol (cysteamine), butylated hydroxyanisole (BHT), or sodium sulfate and derivatives thereof, including salts and sulfurous acid salts thereof. Pentetic acid (DTPA) an antioxidant stabilizer, may also act as a chelator. Another non-limiting example of a chelator includes edetic acid (EDTA).

The liquid, ready-to-use, aqueous composition described herein contains about 0.1 to about 50 mg/mL of the stabilizer. In some aspects, the liquid, ready-to-use, aqueous composition contains about 0.1, about 1, about 5, about 10, about 20, about 25, about 30, about 40, or about 50 mg/mL of the stabilizer. In other aspects, the liquid, ready-to-use, aqueous composition contains about 1 to about 50, about 1 to about 40, about 1 to about 30, about 1 to about 25, about 1 to about 20, about 1 to about 10, about 1 to about 5, about 5 to about 50, about 5 to about 40, about 5 to about 30, about 5 to about 25, about 5 to about 20, about 5 to about 10, about 10 to about 50, about 10 to about 40, about 10 to about 30, about 10 to about 25, about 10 to about 20, about 20 to about 50, about 20 to about 40, about 20 to about 30, about 20 to about 25, about 25 to about 50, about 25 to about 40, about 25 to about 30, about 30 to about 50, about 30 to about 40, or about 30 to about 50 mg/mL of the stabilizer. In further aspects, the liquid, ready-to-use, aqueous composition contains about 1 to about 40 mg/mL of the stabilizer. In other aspects, the liquid, ready-to-use, aqueous composition contains about 5 to about 30 mg/mL of the stabilizer. In further aspects, the liquid, ready-to-use, aqueous composition contains about 10 to about 25 mg/mL of the stabilizer.

The liquid, ready-to-use, aqueous composition described herein contains about 0.1 to about 50 mg/mL of mannitol. In some aspects, the liquid, ready-to-use, aqueous composition contains about 0.1, about 1, about 5, about 10, about 20, about 25, about 30, about 40, or about 50 mg/mL of mannitol. In other aspects, the liquid, ready-to-use, aqueous composition contains about 1 to about 50, about 1 to about 40, about 1 to about 30, about 1 to about 25, about 1 to about 20, about 1 to about 10, about 1 to about 5, about 5 to about 50, about 5 to about 40, about 5 to about 30, about 5 to about 25, about 5 to about 20, about 5 to about 10, about 10 to about 50, about 10 to about 40, about 10 to about 30, about 10 to about 25, about 10 to about 20, about 20 to about 50, about 20 to about 40, about 20 to about 30, about 20 to about 25, about 25 to about 50, about 25 to about 40, about 25 to about 30, about 30 to about 50, about 30 to about 40, or about 30 to about 50 mg/mL of mannitol. In some aspects, the liquid, ready-to-use, aqueous composition contains about 1 to about 40 mg/mL of mannitol. In other aspects, the liquid, ready-to-use, aqueous composition contains about 5 to about 30 mg/mL of mannitol. In further aspects, the liquid, ready-to-use, aqueous composition contains about 10 to about 25 mg/mL of mannitol.

In other embodiments, the pharmaceutically acceptable excipient is a tonicity adjustor. Osmolality is the concentration of a solution expressed as the total number of solute particles per a given mass, taking all the solute concentrations into account, and is expressed in osmol/kg. Tonicity is the measure of the effective atmospheric gradient and the ability of an extracellular solution to move into or out of a cell by osmosis, only considering solutes which fail to pass through a semipermeable membrane, as they are the only solutes having an influence on the osmotic pressure gradient. Tonicity is the measure of the osmotic pressure gradient. In certain embodiments described herein, the osmolality of the liquid, ready-to-use, aqueous composition is about 200 to about 1000 mOsmol/Kg. In other embodiments, the osmolality of the liquid, ready-to-use, aqueous composition is about 200 to about 700, about 200 to about 600, about 275 to about 600, or about 275 to about 550, about 300 to about 550, or about 300 to about 600 mOsmol/Kg.

The tonicity adjuster acts to provide and maintain a stable tonicity for the liquid, ready-to-use, aqueous composition disclosed herein. In some embodiment, tonicity adjustors also function as a non-aqueous solvent, a solubilizer, and/or a stabilizer. In such instances, tonicity adjusters may be used at concentrations higher than needed for tonicity if their primary purpose is stabilization or may be used at concentrations higher than needed for stabilization if their primary purpose is tonicity adjustment.

In some aspects, the tonicity adjuster is a pharmaceutically acceptable inorganic chloride, e.g., potassium chloride, sodium chloride, magnesium chloride or calcium chloride. In other aspects, the tonicity adjuster is sodium chloride. In further aspects, the tonicity adjuster is 0.9% NaCl. In yet other aspects, the tonicity adjuster is a saccharide such as mannitol, sorbitol, lactose, trehalose, raffinose, dextrose, maltose, galactose, sucrose, or polysucrose. In still further aspects, the tonicity adjuster is mannitol. In yet other aspects, the tonicity adjuster is 5% D-mannitol. In other aspects, the tonicity adjuster is a non-aqueous polar aprotic or protic materials such as polyethylene glycol, N,N-dimethylacetamide, N-methyl pyrrolidone, glycerol, propylene glycol, ethanol, t-butyl alcohol, benzyl alcohol, benzyl benzoate, dimethyl sulfoxide, or glycerol. In further aspects, the tonicity adjuster is a polymer such as polyethylene glycol, polygalacturonic acid, galacturonic acid, polyvinylpyrrolidine (PVP), for example, PEG 300, PEG 400, PEG 3350, PEG 6000, or PEG 8000. In still other aspects, the tonicity adjuster is an amino acid such as lysine, arginine, glycine, methionine, or other amino acids. In yet further aspects, the tonicity adjuster is a cyclodextrin such as dextran, Ficoll, and polyvinylpyrrolidone, and other similar excipients and combinations of these agents.

In particular embodiments, the tonicity adjuster used in the present liquid, ready-to-use, aqueous compositions is dimethyl sulfoxide. The tonicity adjuster can be present in amounts of about 0.1% to about 10% (v/v), based on the volume of the liquid, ready-to-use, aqueous composition. In some aspects, the liquid, ready-to-use, aqueous composition contains about 1 to about 7.5% (v/v), or about 2% to about 5% (v/v) mL of the tonicity adjuster, based on the volume of the composition.

In particular embodiments, the tonicity adjuster used in the present liquid, ready-to-use, aqueous compositions is mannitol. In other aspects, the composition contains about 0.1 to about 50 mg/mL of the tonicity adjuster, based on the weight of the liquid, ready-to-use, aqueous composition. In further aspects, the liquid, ready-to-use, aqueous composition contains about 1 to about 40 mg/mL about 5 to about 30 mg/mL of the liquid, ready-to-use, aqueous composition, from about 10 to about 25 mg/mL of the tonicity adjuster, based on the weight or volume of the liquid, ready-to-use, aqueous composition.

The liquid, ready-to-use, aqueous composition described herein contain at least one buffer. The buffer acts to maintain and stabilize the pH of the aqueous liquid ready-to-use compositions at a desired pH and thereby contribute to chemical stability of the compositions. Buffering agents useful in the preparation of the liquid, ready-to-use, aqueous compositions described herein include, but are not limited to, those buffers which are suitable to provide a stabilized solution pH of from about 4 to about 7.5. In some aspects, the buffer provides a pH of about 4 to about 7.5, or such as about 4 to about 6, or such as about 5.5 to about 6, or such as about 5.25 to about 5.75.

Such buffers include, for example: tartaric acid buffers such as sodium tartrate/tartaric acid buffers; lactate buffers, such as sodium lactate/lactic acid buffers; ascorbic acid buffers such as sodium ascorbate; citrate buffers such as sodium citrate/citric acid buffers; acetate buffers such as sodium acetate, potassium acetate buffers); bicarbonate buffers such as sodium bicarbonate/carbonic acid buffers; succinate buffers such as sodium succinate buffers; benzoate buffers such as sodium benzoate buffers; phosphate buffers such as sodium phosphate buffers; and other buffers well known to those of skill in the art. Buffers can be present in concentrations of about 0.1 mM to about 50 mM, or about 0.5 mM to about 40 mM, or about 1 mM to about 25 mM. In some embodiments, a buffer is sodium acetate/acetic acid buffer, in concentrations of about 1 mM to about 25 mM, or about 2 mM to about 20 mM, or about 5 mM to about 20 mM. In other embodiments, the buffer is 10 mM sodium acetate.

In one embodiment of any of the liquid, ready-to-use, aqueous compositions described herein, the composition comprises at least one acetate buffer. In a further embodiment of any of the liquid, ready-to-use, aqueous compositions described herein, the composition comprises sodium acetate (e.g., about 0.82 mg/mL sodium acetate).

In a further embodiment of any of the liquid, ready-to-use, aqueous compositions described herein, the composition comprises sodium acetate (e.g., about 0.82 mg/mL sodium acetate) and dimethyl sulfoxide (e.g., about 20 mg/mL or about 22 mg/mL dimethyl sulfoxide).

The liquid, ready-to-use, aqueous composition may also contain pharmaceutically acceptable pH adjusting agents. pH adjusting agents may be included to make adjustments to the pH of starting, intermediate or final solutions. Examples of pH adjusting agents include mineral acids, organic acids, their conjugate bases, alkali metal salts, ammonium species, hydroxy species, and the like. Such agents will be well known to those of skill in the art. In some embodiments, the pH adjusting agent is sodium hydroxide. In other embodiments, the pH adjusting agent is hydrochloric acid.

In some embodiments, the liquid, ready-to-use, aqueous compositions further comprise one or more pharmaceutically acceptable excipients, carriers, diluents, fillers, salts, further buffers, further stabilizers, further solubilizers, and other materials known in the art. The preparation of pharmaceutically acceptable formulations and pharmaceutically acceptable injectable formulations containing these materials is described in, e.g., *Remington's Pharmaceutical Sciences*, 18$^{th}$ Edition, ed. A. Gennaro, Mack Publishing Co. Easton, Pa., (1990); and Nema, et al., PDA J. Pharm. Sci. Tech., 51(4), (1997), 166-171, the contents of which are incorporated by reference herein.

In certain embodiments, the disclosure provides liquid, ready-to-use, aqueous compositions comprising bortezomib, mannitol, dimethyl sulfoxide, sodium acetate, and water. In some aspects, the liquid, ready-to-use, aqueous composition contains about 1 mg/mL of bortezomib. In other aspects, the liquid, ready-to-use, aqueous composition contains about 10 mM of sodium acetate, about 10 mg/mL of mannitol, about 20 mg/mL of DMSO, and optionally hydrochloric acid, sodium hydroxide, or a combination thereof. In further aspects, the liquid, ready-to-use, aqueous composition has a pH of about 5.5 to about 6. In still other aspects, the liquid, ready-to-use, aqueous composition contains about 2.5 mg/mL of bortezomib. In yet further aspects, the liquid, ready-to-use, aqueous composition contains about 10 mM of sodium acetate, about 25 mg/mL of mannitol, about 22 mg/mL of DMSO, and water, and optionally hydrochloric acid, sodium hydroxide, or a combination thereof. In other aspects, the liquid, ready-to-use, aqueous composition has a pH of about 5.25 to about 5.75.

In further embodiments, the disclosure provides intravenous, ready-to-use dosage forms comprising bortezomib, mannitol, dimethyl sulfoxide, sodium acetate, and water. In some aspects, the intravenous, ready-to-use dosage form contains about 1 mg/mL of bortezomib. In other aspects, the intravenous, ready-to-use dosage form contains about 2.5 mg/mL of bortezomib. In further aspects, the intravenous, ready-to-use dosage form comprises about 10 mM of sodium acetate, about 10 mg/mL of mannitol, about 20 mg/mL of DMSO, and water, and optionally hydrochloric acid, sodium hydroxide, or a combination thereof. In yet other aspects, the intravenous, ready-to-use dosage form has a pH of about 5.5 to about 6.

In other embodiments, the disclosure provides subcutaneous, ready-to-use dosage forms, comprising bortezomib, mannitol, dimethyl sulfoxide, sodium acetate, and water. In certain aspects, the subcutaneous, ready-to-use dosage form contains about 1 mg/mL of bortezomib. In other aspects, the subcutaneous, ready-to-use dosage form contains about 2.5 mg/mL of bortezomib. In further aspects, the subcutaneous, ready-to-use dosage form contains about 10 mM of sodium acetate, about 25 mg/mL of mannitol, about 22 mg/mL of DMSO, and water, and optionally hydrochloric acid, sodium hydroxide, or a combination thereof. In yet other aspects, the subcutaneous, ready-to-use dosage form has a pH of about 5.25 to about 5.75.

In one embodiment, the ready-to-use compositions described herein are free or substantially free of antimicrobial preservatives, such as parabens (e.g., methylparaben and propylparaben).

Stability Profiles

The compositions described herein are storage stable aqueous liquid ready-to-use compositions. The degradation of the active ingredient, as well as the formation of various impurities is controlled by the composition to a minimal level. Stability testing was performed at the long-term stability condition (2-8° C.) as well as the accelerated stability condition (25±2° C./60±5% RH) for refrigerated products. At each time point, the bortezomib content (assay) and the impurity profile was determined using an HPLC procedure, and a bortezomib reference standard. The HPLC method utilizes a reverse phase column with an aqueous formic acid/acetonitrile and aqueous formic acid/methanol mobile phase gradient and UV/PDA detector at a wavelength of about 270 nm. The bortezomib content (assay) is determined as the ratio of the peak area response for bortezomib in the sample versus that of a bortezomib standard (adjusted for its weight and potency) and reported as the percent of the bortezomib nominal concentration (1 mg/mL or 2.5 mg/mL). The impurities are determined as the ratio of the peak area response of each impurity in the sample versus that of a bortezomib standard (adjusted for its weight and potency), its relative response factor (relative to bortezomib if different) and reported as a percent of the bortezomib nominal concentration (label claim of 1 mg/mL or 2.5 mg/mL).

Under refrigerated storage conditions (2-8° C.), for example, the assay of bortezomib in the present liquid, ready-to-use, aqueous compositions is maintained as at least 90%, or the reduction in assay of bortezomib from the initial assay is less than 10%, after storage at 2-8° C. for up to about 6 months, or up to about 9 months, or up to about 12 months, or up to 24 months. Under refrigerated storage conditions, for example, the increase in total impurities from the time of manufacture in the present liquid, ready-to-use, aqueous compositions is no more than about 3.5% or volume, based on the total weight or volume of the liquid, ready-to-use, aqueous composition after storage at 2-8° C. for up to about 6 months, or up to about 9 months, or up to about 12 months, or up to 24 months. Under refrigerated storage conditions, for example, the detection of any single impurity in the present liquid, ready-to-use, aqueous compositions is no more than about 1.5% after storage at 2-8° C. for up to about 6 months, or up to about 9 months, or up to about 12 months, or up to 24 months.

Under accelerated storage conditions (25° C./60% RH), for example, the assay of bortezomib in the present liquid, ready-to-use, aqueous compositions is maintained as at least 90%, or the reduction in assay of bortezomib from the initial assay is less than 10%, after storage at 25° C./60% RH for up to about 1 month, or up to about 2 months, or up to about 3 months. Under accelerated storage conditions, for example, the detection of total impurities in the present liquid, ready-to-use, aqueous compositions is no more than about 1% after storage at 25° C./60% RH for up to about 1 month, and no more than about 3.5% for up to about 3 months. Under long term storage conditions, for example, the detection of any single impurity in the present liquid, ready-to-use, aqueous compositions is no more than about 1.5% after storage at 25° C./60% RH for up to about 1 month, or up to about 3 months.

In one embodiment, the liquid, ready-to-use, aqueous compositions described herein are stored under refrigeration at about 2 to about 8° C. and protected from light.

Processes for Preparing Bortezomib Compositions

The bortezomib liquid, ready-to-use, aqueous composition compositions described herein are produced by methods described in detail below. The volumes and amounts of materials will vary depending on the purpose of the liquid, ready-to-use, aqueous composition and the desired batch size. Aqueous liquid ready-to-use, aqueous compositions for injection can be prepared for intravenous or subcutaneous administration, which may require different concentrations of active ingredient or other excipients. Formulations prepared and administered for intravenous injection are generally less concentrated than formulations prepared and administered for subcutaneous injection.

In the general method of making bortezomib liquid, ready-to-use, aqueous composition compositions, two or more solutions may be prepared individually and mixed together for the final liquid, ready-to-use, aqueous composition. The use of the term "first" or "second" solution(s) below does not imply any particular order of preparation of these solutions and the terms are used only to distinguish them from each other. The "first" solution may be prepared after the "second" solution (s).

The disclosure, thus, provides processes of preparing a liquid, ready-to-use aqueous composition comprising bortezomib. The process includes combining bortezomib and a non-aqueous solvent to form a first solution. The process also includes combining one or more pharmaceutically acceptable excipients with water to form a second solution. The first solution and second solution are then combined using skill in the art. The combined solutions are then diluted with a volume of water sufficient to form the liquid composition comprising at least 50% water by volume, based on the total volume of the liquid composition.

The pH of the first solution, second solution, or combined solution may then be adjusted. In other aspects, the pH of the first solution is adjusted. In further aspects, the pH of the second solution is adjusted. In still other aspects, the pH of the combined solutions is adjusted. In yet further aspects, the pH of the one or more solutions is adjusted to a pH of about 4 to about 7. In other aspects, the pH of the one or more solutions is adjusted to a pH of about 4 to about 7, about 4 to about 6.5, about 4 to about 6, about 4 to about 5.5, about 4 to about 5, about 4 to about 4.5, about 4.5 to about 7, about 4.5 to about 6.5, about 4.5 to about 6, about 4.5 to about 5.5, about 4.5 to about 5, about 5 to about 7, about 5 to about 6.5, about 5 to about 6, about 5 to about 5.5, about 5.5 to about 7, about 5.5 to about 6.5, about 5.5 to about 6, about 6 to about 7, about 6 to about 6.5, or about 6.5 to about 7. The pH is adjusted using a buffer as described herein.

The process may further include adding the liquid, aqueous composition to a container. Since the container may contain oxygen, it may be removed using skill in the art. In some aspects, the oxygen is removed from the headspace of the container using evacuation. Desirably, the oxygen content of the gas in the headspace is less than about 5% by volume after evacuation. In some aspects, the oxygen content of the gas in the headspace is less than about 4%, about 3%, about 2% or about 1% by volume. Thereafter, the process may include adding nitrogen or a noble gas to the container.

For example, a target final batch volume of 100 mL of 2.5 mg/mL bortezomib solution, with 2% non-aqueous solvent, containing 25 mg/mL solubilizer/stabilizer, and 10 mM buffer can be prepared as follows. A first solution is prepared, having a volume as a specific predetermined fraction of the final target volume the non-aqueous solvent. The volume of the non-aqueous solvent is chosen to result in the desired final concentration. For example, assuming a target final batch volume of 100 mL and a target final non-aqueous solvent concentration of 2% by volume, this calls for a target non-aqueous solvent volume of 2 mL. Thus, the first solution in this example can contain up to 2 mL of the non-aqueous solvent. In some embodiments, the entire target amount of the non-aqueous solvent is put into, or used as, the first solution. In other embodiments, a known portion of the target amount of the non-aqueous solvent is put into the first solution, and the remainder of the target amount of the non-aqueous solvent is added during subsequent steps.

In the present example of final batch volume of 100 mL, and a target final bortezomib concentration of 2.5 mg/mL, a target bortezomib amount of 250 mg is called for (adjusted as may be necessary for as-is potency). The term "as-is potency" as used herein refers to the percent of the bortezomib as the monomeric boronic acid that is in the bortezomib drug substance which may also contain water, counterions, bortezomib salts, bortezomib derivatives, and residual solvents. Thus, the first solution in this example can contain up to 250 mg of bortezomib. In some embodiments, the entire target amount of bortezomib is put into the first solution. In other embodiments, a portion of the target amount of the bortezomib is put into the first solution, and the remainder is added during subsequent steps. The first solution (bortezomib concentrated premix solution) is stirred to ensure complete solubilization of the bortezomib.

Similarly, the target amounts (or known portions thereof) of solubilizer, stabilizer, and buffer are chosen to result in the desired final tonicity adjuster/stabilizer and buffer concentration. A second solution or solutions is prepared by dissolving these components, individually or together, in water, optionally adjusting the pH with pH adjusting agent, if desired, and are combined with the first solution. According to the present example of a target final batch volume of 100 mL, a target final tonicity adjuster/stabilizer concentration of 25 mg/mL calls for a target tonicity adjuster/stabilizer amount of 2500 mg. In the same way, a target final batch volume of 100 mL and a target final buffer concentration of 10 mM calls for a target buffer amount which relates to the molecular weight of the buffer and the target batch volume; for example, for 10 mM sodium acetate, the target amount is 82 mg (on anhydrous basis). The second solution(s) may be prepared in a fractional volume of water based on the target final batch volume, for example, 50%, or a lesser amount of a more concentrated buffer solution, or a greater amount of a less concentrated solution. In some embodiments, the entire target amount of tonicity adjuster/stabilizer and/or buffer are combined with (or used to create) the second solution. In other embodiments, portions of the target amounts of the solubilizer, stabilizer, tonicity adjuster, and/or buffer are combined with (or used to create) the second solution(s), and the remainder is added at subsequent steps.

The solution resulting from combination of excipients contains all desired components of the target final batch solution, albeit in higher concentrations than their desired final batch concentrations. Dilution, for example aqueous dilution, of the first solution of excipients may be carried out to achieve the target final batch volume, for example, in an appropriate volumetric vessel. The pH of the solution can be adjusted using pharmaceutically acceptable pH-adjusting agents as the dilution is carried out. The solution can be adjusted to a pH of for example, about 4 to about 7, or from about 4.5 to about 6.5, or from about 5.5 to 6.5. Filtration, for example, sterile filtration, can be carried out and the pH checked again to ensure stability. Packaging into containers, such as vials, and closure of the containers, e.g., stoppering of the containers can be carried out subsequently.

The components used in the liquid, ready-to-use, aqueous composition can be assembled in a controlled atmosphere, e.g., under low-oxygen conditions, so that the solutions contain minimal oxygen and thus oxidation reactions and resulting degradation are avoided. The entire compounding operation can be performed in a controlled atmosphere vessel, with prior degassing (e.g., removal of oxygen) of any other solutions combined with the first solution. For example, the oxygen levels in the atmosphere to which the components are exposed can be less than 5%, or less than 3%, or less than 2% or less than 1% by volume. The oxygen levels can be determined by measuring the molecular composition of the headspace in a container containing the liquid, ready-to-use, aqueous compositions.

In particular examples, the light levels to which the liquid, ready-to-use, aqueous compositions are exposed can also be controlled, to provide low-light conditions, as light can contribute to instability of bortezomib solutions. These may include limiting the light-exposure of the product during manufacturing by keeping the product in closed containers as much as practical, controlling the ambient light level during manufacturing, and/or using lights with long wavelengths (such as more than 500 nm).

Devices for Storing the Bortezomib Compositions

The bortezomib compositions described herein may be stored in suitable containers. In some aspects, the containers are glass or plastic. In some aspects, the container is a vial, syringe, infusion bag, or elastomeric device, among others. The container may be sealed using heat or closed with a suitable cap. The container is typically substantially filled, leaving a headspace. In some aspects, the headspace contains an inert gas, such as a noble gas. In other aspects, the headspace contains nitrogen gas.

Methods of Using Bortezomib Compositions

The aqueous liquid ready-to-use aqueous bortezomib compositions may be used to for any condition for which bortezomib is used. Thus, the disclosure provides methods of using the liquid, ready-to-use, aqueous compositions, the intravenous dosage forms, or the subcutaneous dosage forms described herein.

The disclosure also provides methods for treating cancer in patients in need of such therapy by administering the liquid, ready-to-use, aqueous compositions, the intravenous dosage forms, or the subcutaneous dosage forms as described herein to the patient. In some embodiments, the cancer is multiple myeloma. In other embodiments, the cancer is mantle cell lymphoma therapy. In further embodiments, the cancer is relapsed mantel cell lymphoma. The liquid, ready-to-use, aqueous compositions described herein may be administered by parenteral means such as subcutaneous, intradermal, intramuscular, intraperitoneal, intravenous, intraarticular, or intramedullar. In some aspects, administration is subcutaneous. In other aspects, administration is intravenous. Thus, the liquid ready-to-use compositions of bortezomib disclosed herein may be administered by injection, for example, intravenously or subcutaneously. In some aspects, the liquid, ready-to-use, aqueous composition are administered intravenously and the administered concentration of bortezomib is about 1 mg/mL. In other aspects, the liquid, ready-to-use, aqueous composition are administered intravenously and the administered concentration of bortezomib is about 2.5 mg/mL. In further aspects, the liquid, ready-to-use, aqueous composition are administered subcutaneously and the administered concentration of bortezomib is about 2.5 mg/mL. In yet other aspects, the liquid, ready-to-use, aqueous composition are administered subcutaneously and the administered concentration of bortezomib is about 1 mg/mL.

In one embodiment, the liquid, ready-to-use, aqueous composition (for instance, a composition having a bortezomib concentration greater than 1 mg/mL, such as a concentration of about 2.5 mg/mL) is administered intravenously without any further dilution.

The aqueous liquid ready-to-use aqueous bortezomib compositions can be stored at 2-8° C., or up to 72 hours at about 25° C. once removed from the refrigerator. The product may also be stored for up to 8 hours in a syringe; however, total storage time may be kept less than about 72 hours at 25° C.

The term parenteral as used herein includes subcutaneous, intracutaneous, intravenous, intramuscular, intraarticular, intraarterial, intrasynovial, intrasternal, intrathecal, intralesional and intracranial injection or infusion techniques.

The liquid, ready-to-use, aqueous composition may be in the form of a sterile injectable preparation, for example, as a sterile injectable aqueous or oleaginous suspension. The term "sterile" as used herein refers to a solution that is substantially free, from bacteria or other living microorganisms. In general, the term "sterile" refers to a solution that contains no bacterial or other living microorganisms, i.e., zero colony-forming units by volume, based on the volume of the liquid, ready-to-use, aqueous composition.

One embodiment is a method for administering bortezomib to a patient in need thereof, comprising intravenously administering a liquid, ready-to-use aqueous composition comprising about 0.5 to about 5 mg/mL of bortezomib, mannitol, sodium acetate and dimethyl sulfoxide, where the ready-to-use composition is prepared by a process comprising adding a first solution of bortezomib dissolved in dimethyl sulfoxide to a second solution comprising mannitol, sodium acetate, and water, wherein the pH of the ready-to-use composition is about 5 to about 6.

The liquid, ready-to-use, aqueous composition may be administered intravenously at a starting dose of 1.3 mg/m². The liquid, ready-to-use, aqueous composition described herein may be administered as described in section 2 of the prescribing information for bortezomib intravenous solution (New Drug Application No. 215331) and the composition may be that described in section 11 of the prescribing information. The entire contents of the prescribing information for the bortezomib intravenous solution described in New Drug Application No. 215331 is hereby incorporated by reference.

In the following examples, efforts have been made to ensure accuracy with respect to numbers used (e.g., amounts, temperature, etc.) but some experimental error and deviation should be accounted for. Unless indicated otherwise, temperature is in degrees C., pressure is at or near atmospheric.

EXAMPLES

Example 1: Solubility of Bortezomib in Non-Aqueous Solvents

The goal of the formulation development was stable ready-to-use primarily aqueous liquid formulations of bortezomib at a concentration of 1 mg/mL or 2.5 mg/mL. The solubility of bortezomib in select non-aqueous solvents was determined to understand if any of these solvents may be useful (as a co-solvent with water) at low concentrations in the final formulation.

Approximately 25 mg of bortezomib was added to a suitable container. An initial volume of 0.5 mL of the non-aqueous solvent was added and the mixture stirred for 5 minutes. The appearance of the solution was recorded. If the bortezomib was fully dissolved, the solubility was reported as >50 mg/mL. If the bortezomib was not fully dissolved, additional volume of solvents were added in 0.25 mL increments with mixing for 5 minutes after each addition, and recording the appearance of the solution, until the bortezomib was fully dissolved, up to a total volume of 10 mL. The results are shown in Table 1 below.

TABLE 1

Estimated Solubility of Bortezomib in Select Non-aqueous Solvents

| Non-aqueous Solvent | Observation | Estimated Solubility (mg/mL) |
|---|---|---|
| propylene glycol | Approximately 7 mL of solvent needed | ~3.6 |
| alcohol (ethanol) | Approximately 5.5 mL of solvent needed | ~4.5 |
| polyethylene glycol 400 | No significant dissolution observed up to 10 mL | <2.5 |
| glycerol | No significant dissolution observed up to 10 mL | <2.5 |
| N-methyl pyrrolidone (NMP) | Completely dissolved after 1 mL | >25 |
| dimethyl sulfoxide (DMSO) | Completely dissolved after 0.5 mL | >50 |
| benzyl alcohol | Completely dissolved after 0.5 mL | >50 |

Because non-aqueous solvents are not typically preferable for ready-to-use parenteral products in the art, e.g., for the reasons discussed earlier, the goal was to limit the concentration of non-aqueous solvent in the final formulation to low levels that are generally considered safe. Therefore, solvents that showed a solubility of >50 mg/mL were evaluated. The initial screening showed acceptable solubility in two solvents: namely, benzyl alcohol (>50 mg/mL) and dimethyl sulfoxide (>50 mg/mL). Benzyl alcohol and DMSO were selected for further evaluation, e.g., at lower concentrations of these solvents in aqueous systems.

Example 2: Formulations with Low Concentrations of Benzyl Alcohol

Initial formulation experiments with low concentrations of various non-aqueous solvents were conducted targeting a bortezomib concentration of 2.5 mg/mL. Attempts to solubilize bortezomib were conducted using low concentrations of benzyl alcohol (2% v/v), or dimethyl sulfoxide (5% v/v), or a combination of these solvents. Higher concentrations of benzyl alcohol were not used because of the immiscibility of benzyl alcohol with water at concentrations greater than the solubility of benzyl alcohol in water (35 mg/mL). For these formulations, the non-aqueous solvent was added to bortezomib to dissolve it, followed by addition of water to the bortezomib-solvent mixture. Although bortezomib could at least partially or completely be dissolved in the non-aqueous solvent, it precipitated after addition of water and was not completely dissolved even after extensive mixing (>3 hours), indicating that the solubility of bortezomib was insufficient in the matrix at these even significant amounts of non-aqueous solvent (up to 50% as a combination of NMP, DMSO, ethanol and benzyl alcohol). Heating the solution up to 70° C. also failed to dissolve the precipitated bortezomib, and a pink color formed indicating degradation of the active. Further attempts at using benzyl alcohol (2% v/v) alone or in combination with DMSO (2% v/v) or alcohol (2% v/v) were also similarly unsuccessful. Benzyl alcohol (2% v/v) in buffered sodium acetate solutions (0.1 M sodium acetate at pH 4, 5, 6) alone or in combination with propylene glycol (3 mg/mL, pH 6) were also unsuccessful.

Example 3: Formulations with Low Concentrations of DMSO in Water

Various concentrations of DMSO were explored as the non-aqueous component of the formulation (2% v/v to 5% v/v in water). Bortezomib was first completely dissolved in the batch volume of DMSO to form a concentrated "premix" solution prior to making up the batch to the target concentration (2.5 mg/mL) with water. This was done to facilitate the subsequent dissolution of bortezomib in the aqueous component. The pH values of the formulations were all approximately 7. All formulations with DMSO resulted in a clear solution with visually complete dissolution of the active.

The effect of pH on bortezomib formulations using a low concentration of DMSO in water (4.5% v/v DMSO for the 2.5 mg/mL strength and 1% v/v DMSO for the 1 mg/mL strength) was then assessed. In each case, the bortezomib was first fully dissolved in the batch quantity of DMSO to form a concentrated premix solution, which was then added to water, and the pH adjusted with sodium hydroxide and/or hydrochloric acid to pH ranging from 4 to 8.5. In each case, the batch was successful in achieving a clear solution with complete dissolution of the active. Because oxidative degradation is a significant degradation pathway for bortezomib, filled vials were overlayed with nitrogen. These batches were placed on stability at accelerated (25° C.) and long-term storage conditions (2-8° C.). All batches formulated at 2.5 mg/mL showed formation of crystals after 1 month at 25° C., while the batches at 1 mg/mL remained clear with no crystal formation (physical stability) for at least 2 months (last observation point). Although the 2.5 mg/mL formulations were not physically stable at 25° C., chemical stability, based on analysis after 2 months at 25° C., stability was poor at pH 4 and pH 8.5 for both strengths, with good stability being observed at pH 5.5 for the 2.5 mg/mL strength and pH 5.5 and 7 for the 1 mg/mL strength.

TABLE 2

Effect of pH on Chemical Stability of DMSO-based Aqueous Formulations

| Bortezomib Strength | Formulation | pH* | Total Impurities after 2 months at 25° C. (%) |
|---|---|---|---|
| 2.5 mg/mL | 4.5% (v/v) DMSO in water | 4 | 13.71 |
|  |  | 5.5 | 1.07 |
|  |  | 7 | 5.91 |
|  |  | 8.5 | 31.59 |
| 1 mg/mL | 1% (v/v) DMSO in water | 4 | 7.83 |
|  |  | 5.5 | 0.52 |
|  |  | 7 | 1.18 |
|  |  | 8.5 | 12.48 |

*pH adjusted with hydrochloric acid or sodium hydroxide

Example 4—Solubility Study: Direct Addition of Bortezomib to the Non-Aqueous Solvent Because of the inability to maintain physical stability of bortezomib formulations at 2.5 mg/mL at low concentrations of non-aqueous solvents when bortezomib is added directly to the co-solvent system, the equilibrium solubility of bortezomib in particular solvents and solvent mixtures was determined by an HPLC method. Because pH appeared to influence chemical stability, sodium acetate or sodium phosphate were included in these matrixes as buffers, and the effect of pH on solubility was also assessed.

A bortezomib sample (between 10 and 50 mg) was placed in a suitable glass container and added to 5 mL of a solvent system as defined below in Table 3. The components were mixed (by shaking the glass container), and the mixture was observed. If the mixture was a clear solution (i.e., bortezomib completely soluble), an additional amount of bortezomib was added until an excess of undissolved bortezomib was present in the glass container. The suspension was allowed to equilibrate for 24 hours at room temperature while being protected from light. After the incubation, the solution phase was removed from the container into a clean vial by filtration through a 0.45 micron syringe filter, and the filtrate was assayed for bortezomib content using an HPLC procedure, and a bortezomib standard.

One mL aliquots of the filtrate (saturated solution) were subjected to three freeze-thaw cycles of 24 hours at −20° C. and 24 hours at 25° C. each, with visual examination after each cycle. Absence of precipitation after the three cycles was used as an index of physical stability of the formulation upon long-term storage. The results are shown in Table 3 below.

TABLE 3

Solubility of Bortezomib Added Directly to Solvent System

| # | Solvent | Solubility (mg/mL) | Physical Appearance of Saturated Solution After Freeze-Thaw Cycles | | |
|---|---|---|---|---|---|
| | | | Cycle #1 | Cycle #2 | Cycle #3 |
| S1 | 50 mM sodium acetate, pH 4 | 0.33 | Clear solution | | |
| S7 | 50 mM sodium acetate, pH 4 + 2% DMSO (v/v) | 0.97 | Undissolved active present | | |
| S4 | 50 mM sodium acetate, pH 4 + 4.5% DMSO (v/v) | 0.88 | Undissolved active present | | |
| S2 | 50 mM sodium acetate, pH 5.5 | 0.42 | Clear solution | | |
| S14 | 50 mM sodium acetate + 2% DMSO (v/v) + 6% propylene glycol (v/v), pH 5.5 | 0.56 | Undissolved active present | | |
| S5, S8 | 50 mM sodium acetate, pH 5.5 + 4.5% DMSO (v/v) | 0.99, 0.46 | Undissolved active present | | |
| S10, K7L* | 50 mM sodium acetate + 25 mg/mL mannitol, pH 5.5 | 1.4, 0.51 | Clear solution | | |

TABLE 3-continued

Solubility of Bortezomib Added Directly to Solvent System

| # | Solvent | Solubility (mg/mL) | Physical Appearance of Saturated Solution After Freeze-Thaw Cycles | | |
|---|---------|--------------------|--------|--------|--------|
| | | | Cycle #1 | Cycle #2 | Cycle #3 |
| S11, K8L* | 50 mM sodium acetate + 25 mg/mL mannitol + 2% DMSO (v/v), pH 5.5 | 1.7, 0.69 | Clear solution | | |
| K9L* | 50 mM sodium acetate + 25 mg/mL mannitol + 4.5% DMSO (v/v), pH 5.5 | 0.77 | Clear solution | | |
| K10L* | 50 mM sodium acetate + 50 mg/mL mannitol + 2% DMSO (v/v), pH 5.5 | 0.46 | Clear solution | | |
| S3 | 50 mM sodium dihydrogen phosphate, pH 7 | 0.39 | Clear solution | | |
| S6, S9 | 50 mM sodium dihydrogen phosphate, pH 7 + 2% DMSO (v/v) | 0.46, 0.41 | Clear solution | | |
| S12 | 50 mM sodium dihydrogen phosphate, 4.5% DMSO (v/v), pH 8.5 | 0.48 | Clear solution | | |
| S13 | 50 mM sodium dihydrogen phosphate, 2% DMSO (v/v), pH 8.5 | 0.62 | Clear solution | | |

*A second source of pharmaceutical grade bortezomib. The samples with this second source of bortezomib are labeled with a "K" rather than an "S."

One goal of bortezomib formulation development is achieving bortezomib solubility of greater than 1 mg/mL for a formulation suitable for intravenous injection, and solubility greater than 2.5 mg/mL for a formulation suitable for subcutaneous injection. Table 3 shows that the solubilities of bortezomib in buffered aqueous solutions is less than 0.5 mg/mL at the pH range of 4 to 7. This represents an improvement in solubility compared to the values reported for bortezomib in water or buffered aqueous solutions (<0.1 mg/mL) by the suppliers of the pharmaceutical grade bortezomib used in these experiments.

Various non-aqueous solvents alone present in solutions S4-S9 and S12-S14 had modest effects on the solubility at the low concentrations needed to remain at or below the permissible daily exposure (PDE) levels of these solvents which were another goal of the formulations described herein.

Because non-aqueous solvents by themselves did not improve solubility sufficiently to allow formulation at the target concentration of >1 mg/mL, an additional saccharide-based solubilizer, mannitol, was also tried. Table 3 shows that although the solubility of bortezomib as with 25 mg/mL mannitol using pharmaceutical grade bortezomib drug substance from one supplier (S10) was sufficient to potentially allow such formulations to serve as a ready-to-use intravenous injectable product (solubility greater than 1 mg/mL), but not using bortezomib from a second supplier (K7L). For this source of bortezomib, the combination of 25 mg/mL mannitol and low concentrations of DMSO did not significantly improve solubility (K8L, K9L), nor did increasing the mannitol concentration to 50 mg/mL (K10L). None of the test solutions achieved the bortezomib solubility requirement for a ready-to-use formulation suitable for subcutaneous injection (>2.5 mg/mL).

As shown in Table 3, the instant experiments show that the bortezomib, when added directly to the solvent system, does not have the requisite solubility in primarily aqueous solutions with low concentrations of parenterally acceptable non-aqueous solvents to permit formulations for either intravenous (1 mg/mL) or subcutaneous (2.5 mg/mL) use.

Example 5: Solubility of Bortezomib Premixed with Nonaqueous Solvent Before Addition to the Aqueous Component This example was carried out to determine the solubility of bortezomib in particular solvents and solvent systems when the bortezomib is first dissolved in (the batch quantity) of a non-aqueous solvent to form a concentrated solution ("premix"), prior to adding the premix to the aqueous component(s). A bortezomib sample (between 10 and 50 mg) was placed in a suitable glass container and added to a defined volume of a nonaqueous solvent system (if used) as defined below in Table 4, to create a concentrated premix. The premix was subsequently added to enough buffered aqueous solvent to make a final volume of 5 mL, as defined below in Table 4. For example, 50 mg of bortezomib was dissolved in 225 µL of nonaqueous solvent and after ensuring a clear solution resulted, an aqueous solvent system (containing, for example, 50 mM sodium acetate or 50 mM sodium phosphate, at a pH of from about 4 to about 7, and/or containing, for example, a tonicity adjusting agent at about 5 to about 50 mg/mL, or about 0.1% to about 10% by volume) was added to the bortezomib/non-aqueous solvent premix.

The resulting formulation was allowed to equilibrate for 24 hours at room temperature, protected from light. Solubility was determined by filtration through a 0.45 micron filter, and assay of the filtrate for bortezomib content using an HPLC procedure, and a bortezomib standard. One mL aliquots of the filtrate (saturated solution) were subjected to three freeze-thaw cycles of 24 hours at −20° C. and 24 hours at 25° C. each, with visual examination after each cycle. Absence of precipitation after the three cycles was used as an index of physical stability of the formulation upon long-term storage. The results are shown in Table 4 below.

TABLE 4

Solubility of Bortezomib Premixed with Nonaqueous Solvent

| Sample # | Solvent | Solubility (mg/mL) | Physical Appearance of Saturated Solution After Freeze-Thaw Cycles | | |
|----------|---------|--------------------|--------|--------|--------|
| | | | Cycle #1 | Cycle #2 | Cycle #3 |
| K1 | 50 mM sodium acetate, pH 4 + 4.5% DMSO (v/v) | 0.53 | Clear solution | | |

TABLE 4-continued

Solubility of Bortezomib Premixed with Nonaqueous Solvent

| Sample # | Solvent | Solubility (mg/mL) | Physical Appearance of Saturated Solution After Freeze-Thaw Cycles | | |
|---|---|---|---|---|---|
| | | | Cycle #1 | Cycle #2 | Cycle #3 |
| K4 | 50 mM sodium acetate, pH 4 + 2% DMSO (v/v) | 0.40 | Undissolved active present | | |
| K2 | 50 mM sodium acetate, pH 5.5 + 4.5% DMSO (v/v) | 0.80 | Undissolved active present | | |
| K5 | 50 mM sodium acetate, pH 5.5 + 4.5% DMSO (v/v) | 0.66 | Undissolved active present | | |
| K11 | 50 mM sodium acetate, pH 5.5 + 10% DMSO (v/v) | 0.67 | Clear solution | Undissolved active present | |
| K12 | 50 mM sodium acetate, pH 5.5 + 20% DMSO (v/v) | 0.87 | Clear solution | Undissolved active present | |
| K13 | 50 mM sodium acetate, pH 5.5 + 30% DMSO (v/v) | 0.83 | Clear solution | Undissolved active present | |
| K14 | 50 mM sodium acetate, pH 5.5 + 4.5% DMSO (v/v), 10% ethanol USP | 0.89 | Clear solution | Undissolved active present | |
| K15 | 50 mM sodium acetate, pH 5.5 + 4.5% DMSO (v/v), 20% ethanol USP | 1.2 | Clear solution | Undissolved active present | |
| K25 | 50 mM sodium acetate, pH 5.5, 10% DMSO (v/v), 5% ethanol | 1.2 | | Undissolved active present | |
| K33 | 50 mM sodium acetate, 25 mg/mL mannitol, pH 5.5, 2% ethanol | 2.1 | Clear solution | | |
| K32 | 50 mM sodium acetate, pH 5.5 with 2% DMSO (v/v), 1% ethanol | 1 | Clear solution | Undissolved active present | |
| K34 | 50 mM sodium acetate, pH 5.5, 2% ethanol | 0.48 | Clear solution | | |
| K35 | 50 mM sodium acetate, pH 5.5, 2% DMSO (v/v) | 1 | Clear solution | | |
| K16 | 50 mM sodium acetate, pH 5.5 + 25 mg/mL mannitol, 4.5% DMSO (v/v), 10% ethanol USP | 4.5 | Clear solution | | |
| K19 | 50 mM sodium acetate, 25 mg/mL mannitol, pH 5.5 with 2% DMSO (v/v), 2% ethanol | 7.1 | Clear solution | | |
| K20 | 50 mM sodium acetate, 25 mg/mL mannitol, pH 5.5 with 2% DMSO (v/v), 4% ethanol | 6.6 | Clear solution | | |
| K21 | 50 mM sodium acetate, 25 mg/mL mannitol, pH 5.5 with 2% DMSO (v/v), 10% ethanol | 7.2 | Clear solution | | |
| K22, K23L* | 50 mM sodium acetate, 25 mg/mL mannitol, pH 5.5 with 4.5% DMSO (v/v), 10% ethanol | 7.1, 7.1 | Clear solution | | |

TABLE 4-continued

Solubility of Bortezomib Premixed with Nonaqueous Solvent

| Sample # | Solvent | Solubility (mg/mL) | Physical Appearance of Saturated Solution After Freeze-Thaw Cycles | | |
|---|---|---|---|---|---|
| | | | Cycle #1 | Cycle #2 | Cycle #3 |
| K24 | 50 mM sodium acetate, 25 mg/mL mannitol, pH 5.5 with 2% DMSO (v/v), 2% ethanol | 6.8 | Clear solution | | |
| K26, K27L* | 50 mM sodium acetate, 25 mg/mL mannitol, pH 5.5 with 2% DMSO (v/v) | 4.6, 4.3 | Clear solution | | |
| K28, K29L* | 50 mM sodium acetate, 25 mg/mL mannitol, pH 5.5 with 2% DMSO (v/v), 1% ethanol | 4.4, 4.4 | Clear solution | | |
| K30, K31L* | 50 mM sodium acetate, 25 mg/mL mannitol, pH 5.5 with 1% DMSO (v/v), 1% ethanol | 4.1, 4 | Clear solution | | |
| K3 | 50 mM sodium dihydrogen phosphate, pH 7 + 2% DMSO (v/v) | 0.52 | Undissolved active present | | |
| K6 | 50 mM sodium dihydrogen phosphate, pH 7 + 2% DMSO (v/v) | 0.44 | Undissolved active present | | |

*A second source of pharmaceutical grade bortezomib

Because optimal stability was observed around pH 5.5 in aqueous DMSO solutions of Example 4, the bulk of the studies were carried out in sodium acetate buffered aqueous solution at this pH.

As shown in Table 4, formation of a bortezomib premix in the non-aqueous solvent prior to adding it to the aqueous solvent system did not significantly improve solubility compared to direct addition of bortezomib to the co-solvent system, even at fairly high final concentrations of the non-aqueous solvent (samples K1, K2-K6, K5, K11-K15, K25, K32-K35). However, with a solubilizer, in this case 25 mg/mL mannitol, formation of a bortezomib premix in the non-aqueous solvent prior to adding it to the aqueous solvent system significantly and consistently improved bortezomib solubility to >4 mg/mL. Thus, both the formation of the bortezomib premix first in the non-aqueous solvent prior to the addition to the aqueous component, and an aqueous component solubilizer (mannitol) are required to enhance the solubility of bortezomib that is consistent with a physically stable liquid formulation with bortezomib concentrations >1 mg/mL.

Example 6—General Method of Preparation of Exemplary Laboratory Scale Bortezomib Ready-to-Use Formulations The preparation of the concentrated bortezomib premix is performed. The batch quantity of bortezomib is added to a suitable glass container. The batch quantity of the non-aqueous solvent is then added to the bortezomib, and mixed until the bortezomib is completely dissolved. The initial aqueous component is separately prepared by dissolving the other excipients such as buffer, optionally a solubilizer and/or stabilizer, or a tonicity adjuster, in water for injection, which optionally has been degassed by sparging nitrogen through it and adjusting to the desired pH using appropriate pH adjusting agent, if needed. The aqueous component is typically prepared at about double the corresponding concentration(s) in the final formulation; this was typically accomplished by dissolving the excipients in approximately half the batch volume of water. The bortezomib premix is then added to the (concentrated) aqueous component, and mixed. Water is then added to make up to about 80-90% of the batch volume and a final pH adjustment is performed to the target pH using appropriate pH adjusting agent, if needed. After final pH adjustment, the batch is made up to the target batch volume. The batch is then sterile filtered using a 0.2 micron filter, filled into (2-mL, or 3-mL, or 5-mL) USP Type I, optionally amber, glass vials, stoppered with (13-mm or 20-mm) fluoropolymer-coated chlorobutyl rubber stoppers, and sealed with (13-mm or 20-mm) aluminum caps. The fill volume used is typically 3.5 mL for the 1 mg/mL formulations or 1.4 mL for the 2.5 mg/mL formulations (to contain 3.5 mg bortezomib per vial). Because bortezomib is known to be oxidation and light sensitive, compounding and filling is typically carried out in a glove box equilibrated with nitrogen at various residual oxygen levels (typically less than 5%). Light exposure is minimized.

Example 7: Stability Testing of 1 mg/mL Bortezomib Ready-to-Use Formulations without Solubilizer or Stabilizer Because bortezomib solubility in primarily aqueous compositions containing low levels of non-aqueous solvents approached 1 mg/mL (the target concentration for intravenous administration) even without an additional solubilizer (such as mannitol), exemplary formulations were prepared at this concentration containing only active ingredient (bortezomib), non-aqueous solvent at very low concentrations (DMSO), and a buffer. The osmolalities of these formulations was about 313-315 mOsmol/kg, indicating that DMSO, in addition to solubilizing the bortezomib in the premix, was also providing the requisite osmolality. (Note that the theoretical osmolality of 2% (v/v) DMSO in water is approximately 280 mOsmol/kg.)

The long-term stability testing under refrigerated conditions (nominally 5° C., or 2-8° C.), for at least 12 months, and up to 28 months of such formulations is presented in Table 5.

TABLE 5

Bortezomib RTU Formulations at 1 mg/mL without Stabilizer—Long Term Stability Testing at 2-8° C.

| Batch # (pH) | Time Point | Assay (%) | Imp. A | Imp. C | Imp. F | Chiral | Imp. D | Max. Single Unknown | Total |
|---|---|---|---|---|---|---|---|---|---|
| | | | | Impurities (%) | | | | | |
| | | 1 mg/mL bortezomib; 10 mM sodium acetate; 2% (v/v) DMSO | | | | | | | |
| 71 | Initial | 102.1 | 0.01 | 0.29 | 0.02 | 0.03 | 0.15 | 0.33 | 0.96 |
| (pH 5) | 3 M | 80.3 | 0.29 | 9.17 | 0.20 | 0.01 | 11.79 | 11.79 | 23.51 |
| | 5 M | 79.5 | 0.20 | 5.50 | 0.16 | ND | 7.93 | 7.93 | 15.14 |
| | 6 M | 66.7 | 0.44 | 9.40 | 0.43 | ND | 15.16 | 15.16 | 27.86 |
| | 9 M | 54.6 | 0.75 | 15.23 | 0.90 | ND | 25.16 | 25.16 | 51.84 |
| | 12 M | 46.7 | 0.82 | 17.41 | 1.19 | ND | 29.75 | 29.75 | 29.75 |
| | 28 M | 30.0 | 1.35 | 23.41 | 2.46 | ND | 38.01 | 38.01 | 71.01 |
| 72 | Initial | 102.7 | 0.01 | 0.08 | 0.02 | 0.03 | 0.04 | 0.08 | 0.33 |
| (pH 5.5) | 3 M | 105.8 | 0.14 | 2.61 | 0.08 | 0.03 | 2.06 | 0.20 | 5.39 |
| | 5 M | 101.3 | 0.14 | 2.83 | 0.13 | 0.01 | 2.94 | 0.30 | 6.91 |
| | 6 M | 98.6 | 0.24 | 2.59 | 0.19 | 0.02 | 2.96 | 0.23 | 6.54 |
| | 9 M | 43.3 | 0.13 | 0.46 | 0.08 | 0.02 | 0.55 | 0.07 | 1.43 |
| | 12 M | 88.2 | 0.47 | 7.37 | 0.93 | 0.01 | ND | 0.71 | 10.35 |
| | 28 M | 80.4 | 0.56 | 7.99 | 1.19 | ND | 11.09 | 0.61 | 22.09 |
| 73 | Initial | 101.7 | 0.02 | 0.09 | 0.02 | 0.03 | 0.03 | 0.07 | 0.32 |
| (pH 6) | 3 M | 105.4 | 0.12 | 0.43 | 0.05 | 0.04 | 0.20 | 0.02 | 0.90 |
| | 5 M | 109.6 | 0.14 | 0.42 | 0.06 | 0.02 | 0.24 | 0.06 | 0.99 |
| | 6 M | 102.0 | 0.21 | 0.26 | 0.07 | 0.05 | 0.17 | 0.08 | 0.85 |
| | 9 M | 97.6 | 0.30 | 0.54 | 0.15 | 0.05 | 0.40 | 0.08 | 1.56 |
| | 12 M | 93.7 | 0.12 | 0.99 | 9.27 | 0.55 | 0.82 | 2.03 | 14.08 |
| | 28 M | 100.9 | 0.52 | 0.75 | 0.47 | 0.14 | 0.62 | 0.07 | 2.58 |

ND = Not detected

The stability testing under accelerated conditions (25° C. and 60% relative humidity for at least 6 months) of these formulations is presented in Table 6.

TABLE 6

Bortezomib RTU Formulations at 1 mg/mL without Stabilizer—Room Temperature Stability Testing at 25° C.

| Batch # (pH) | Time Point | Assay (%) | Imp. A | Imp. C | Imp. F | Chiral | Imp. D | Max. Single Unknown | Total |
|---|---|---|---|---|---|---|---|---|---|
| | | | | Impurities (%) | | | | | |
| | | 1.0 mg/mL bortezomib; 10 mM acetate; 2% (v/v) DMSO | | | | | | | |
| 71 | Initial | 102.1 | 0.01 | 0.29 | 0.02 | 0.03 | 0.15 | 0.33 | 0.96 |
| (pH 5) | 1 M | 91.4 | 0.33 | 2.82 | 0.33 | 0.03 | 4.41 | 0.46 | 8.90 |
| | 2 M | 86.6 | 0.53 | 3.60 | 0.78 | 0.03 | 5.86 | 0.63 | 12.10 |
| | 3 M | 94.2 | 1.02 | 6.16 | 1.99 | 0.04 | 10.24 | 1.02 | 22.00 |
| | 6 M | 69.8 | 1.45 | 6.18 | 5.63 | 0.03 | 11.05 | 1.04 | 26.22 |
| 72 | Initial | 102.7 | 0.01 | 0.08 | 0.02 | 0.03 | 0.04 | 0.08 | 0.33 |
| (pH 5.5) | 1 M | 99.7 | 0.28 | 0.36 | 0.10 | 0.05 | 0.40 | 0.07 | 1.37 |
| | 2 M | 100.4 | 0.49 | 0.61 | 0.25 | 0.06 | 0.73 | 0.07 | 2.39 |
| | 3 M | 105.4 | 0.85 | 0.97 | 0.50 | 0.08 | 1.13 | 0.08 | 3.84 |
| | 6 M | 97.0 | 1.55 | 0.74 | 1.49 | 0.16 | 1.17 | 0.07 | 5.37 |
| 73 | Initial | 101.7 | 0.02 | 0.09 | 0.02 | 0.03 | 0.03 | 0.07 | 0.32 |
| (pH 6) | 1 M | 99.7 | 0.32 | 0.32 | 0.18 | 0.11 | ND | 0.08 | 1.05 |
| | 2 M | 103.9 | 0.58 | 0.37 | 0.42 | 0.18 | 0.28 | 0.09 | 2.01 |
| | 3 M | 103.1 | 1.03 | 0.43 | 0.72 | 0.31 | 0.31 | 0.09 | 2.97 |
| | 6 M | 93.7 | 1.99 | 0.40 | 2.31 | 0.63 | 0.26 | 0.06 | 5.78 |

ND = Not detected

As shown in Tables 5 and 6, bortezomib formulations which contain 1 mg/mL bortezomib, 10 mM acetate buffer and 2% DMSO, and which do not employ a stabilizer as described herein show undesirable instability upon storage under long-term refrigerated conditions (2-8° C.) at pH 5 and 5.5. At pH 6, generally significantly improved stability was observed (the data point at 12 months is considered an outlier but reported for completeness and potentially vials with inadequate headspace oxygen control). Under room-temperature storage conditions (25° C. and 60% relative humidity), better stability was observed at pH 5.5 and pH 6. These formulations do not contain stabilizers and are not particularly useful as liquid, ready-to-use pharmaceutical formulations.

Example 8: Stability Testing of 1 mg/mL Bortezomib Ready-to-Use Formulations with Stabilizer In the instant example, because mannitol was contemplated as a solubilizer particularly for the 2.5 mg/mL formulations, the stability of bortezomib ready-to-use formulations containing 1 mg/mL bortezomib, 10 mM acetate buffer, 2% DMSO and 10 mg/mL mannitol at pH 5.5 and 6, or 25 mg/mL mannitol at pH 6 was investigated under refrigerated long-term stability (2-8° C.) and accelerated room temperature (25° C.) and the results are presented in Table 7 and Table 8. The osmolalities of these formulations were 323-333 mOsmol/kg, with DMSO still the significant contributor to tonicity in these formulations.

TABLE 7

Bortezomib RTU Formulations at 1 mg/mL with Stabilizer—Long Term Stability Testing at 2-8° C.

| Batch # (pH) | Time Point | Assay (%) | Imp. A | Imp. C | Imp. F | Chiral | Imp. D | Max. Single Unknown | Total |
|---|---|---|---|---|---|---|---|---|---|
| \multicolumn{10}{c}{1 mg/mL bortezomib; 10 mM acetate; 2% (v/v) DMSO; 10 mg/mL mannitol} |
| 69 (pH 5.5) | Initial | 99.7 | 0.02 | 0.02 | 0.02 | ND | 0.03 | 0.07 | 0.26 |
|  | 3 M | 104.9 | 0.14 | 0.26 | 0.03 | 0.04 | 0.21 | 0.10 | 0.84 |
|  | 5 M | 107.9 | 0.16 | 0.21 | 0.03 | 0.02 | 0.21 | 0.07 | 0.75 |
|  | 6 M | 101.9 | 0.22 | 0.29 | 0.05 | 0.03 | 0.32 | 0.08 | 1.04 |
|  | 9 M | 95.4 | 0.30 | 0.32 | 0.06 | 0.02 | 0.39 | 0.08 | 1.23 |
|  | 12 M | 101.5 | 0.41 | 0.45 | 0.09 | 0.03 | 0.59 | 0.09 | 1.74 |
|  | 28 M | 100.4 | 0.43 | 0.81 | 0.15 | 0.07 | 1.05 | 0.07 | 2.70 |
| 70 (pH 6) | Initial | 99.9 | 0.02 | 0.12 | 0.02 | 0.03 | 0.02 | 0.07 | 0.33 |
|  | 3 M | 105.4 | 0.15 | 0.17 | 0.04 | 0.05 | 0.09 | 0.01 | 0.52 |
|  | 5 M | 110.7 | 0.12 | 0.01 | 0.03 | 0.03 | ND | 0.05 | 0.26 |
|  | 6 M | 101.3 | 0.24 | 0.23 | 0.05 | 0.04 | 0.16 | 0.08 | 0.83 |
|  | 9 M | 96.0 | 0.33 | 0.24 | 0.07 | 0.05 | 0.19 | 0.08 | 0.99 |
|  | 12 M | 98.9 | 0.44 | 0.33 | 0.10 | 0.06 | 0.30 | 0.09 | 1.37 |
|  | 28 M | 101.2 | 0.58 | 0.55 | 0.22 | 0.15 | 0.50 | 0.07 | 2.04 |
| \multicolumn{10}{c}{1 mg/mL bortezomib; 10 mM acetate; 2% (w/v) DMSO; 25 mg/mL mannitol} |
| 813 (pH 6.0) | Initial | 99.6 | ND | 0.11 | ND | <0.05 | 0.09 | <0.05 | 0.20 |
|  | 2 M | 98.8 | 0.05 | 0.12 | <0.05 | <0.05 | 0.10 | <0.05 | 0.27 |
|  | 3 M | 99.1 | 0.06 | 0.14 | <0.05 | <0.05 | 0.09 | <0.05 | 0.29 |
|  | 6 M | 100.9 | 0.12 | 0.18 | <0.05 | 0.05 | 0.11 | <0.05 | 0.46 |
|  | 9 M | 101.4 | 0.18 | 0.19 | <0.05 | 0.05 | 0.13 | <0.05 | 0.55 |
|  | 12 M | 101.7 | 0.26 | 0.16 | <0.05 | 0.11 | 0.16 | <0.05 | 0.69 |
|  | 18 M | 98.0 | 0.42 | 0.27 | 0.07 | 0.12 | 0.18 | <0.05 | 1.05 |
|  | 24 M | 96.7 | 0.54 | 0.24 | 0.09 | 0.14 | 0.24 | <0.05 | 1.26 |

ND = Not detected

TABLE 8

Bortezomib RTU Formulations at 1 mg/mL with Stabilizer—Accelerated Stability Testing at 25° C.

| Batch # (pH) | Time Point | Assay (%) | Imp. A | Imp. C | Imp. F | Chiral | Imp. D | Max single | Total |
|---|---|---|---|---|---|---|---|---|---|
| \multicolumn{10}{c}{1 mg/mL bortezomib; 10 mM acetate; 2% (v/v) DMSO; 10 mg/mL mannitol} |
| 69 (pH 5.5) | Initial | 99.7 | 0.02 | 0.02 | 0.02 | ND | 0.03 | 0.07 | 0.26 |
|  | 1 M | 99.3 | 0.31 | 0.17 | 0.06 | 0.07 | ND | 0.08 | 0.75 |
|  | 2 M | 101.7 | 0.52 | 0.38 | 0.13 | 0.09 | 0.34 | 0.09 | 1.66 |
|  | 3 M | 105.8 | 0.97 | 0.40 | 0.30 | 0.16 | 0.53 | 0.07 | 2.48 |
|  | 6 M | 97.4 | 1.77 | 0.37 | 0.75 | 0.29 | 0.55 | 0.07 | 3.97 |
| 70 (pH 6) | Initial | 99.9 | 0.02 | 0.12 | 0.02 | 0.03 | 0.02 | 0.07 | 0.33 |
|  | 1 M | 99.4 | 0.37 | 0.22 | 0.11 | 0.13 | ND | 0.09 | 0.97 |
|  | 2 M | 97.5 | 0.64 | 0.31 | 0.20 | 0.20 | 0.22 | 0.09 | 1.74 |
|  | 3 M | 105.7 | 1.21 | 0.37 | 0.51 | 0.40 | 0.30 | 0.07 | 2.90 |
|  | 6 M | 93.4 | 2.23 | 0.33 | 1.34 | 0.69 | 0.31 | 0.08 | 5.06 |
| \multicolumn{10}{c}{1 mg/mL bortezomib; 10 mM acetate; 2% (w/v) DMSO; 25 mg/mL mannitol} |
| 813 (pH 6) | Initial | 99.6 | ND | 0.11 | ND | <0.05 | 0.09 | <0.05 | 0.20 |
|  | 1 M | 98.4 | 0.43 | 0.13 | 0.08 | 0.22 | 0.11 | <0.05 | 0.97 |
|  | 2 M | 97.6 | 0.79 | 0.13 | 0.14 | 0.37 | 0.12 | 0.06 | 1.65 |
|  | 3 M | 103.4 | 1.23 | 0.16 | 0.22 | 0.54 | 0.14 | 0.09 | 2.45 |
|  | 6 M | 94.3 | 2.25 | 0.20 | 0.42 | 0.89 | 0.17 | 0.15 | 4.15 |

ND = Not detected

As shown in Tables 7 and 8, bortezomib formulations which contain 1 mg/mL bortezomib, 10 mM acetate buffer and 2% DMSO, and 10 mg/mL or 25 mg/mL mannitol at pH 5.5 and 6 were surprising stable under long-term refrigerated conditions (2-8° C.). Under room-temperature storage conditions (25° C. and 60% relative humidity), mannitol containing formulations showed improved stability than without (see Table 6), confirming that mannitol acts as a stabilizer in liquid formulations.

Example 9: Bortezomib Ready-to-Use Formulations at 2.5 mg/mL with Solubilizer/Stabilizer Exemplary formulations containing active ingredient (bortezomib), buffer, solubilizer and tonicity adjuster/stabilizer were prepared at various pH ranging from 4 to 6. The long-term refrigerated stability testing under refrigerated conditions of such formulations is presented in Table 9. In these formulations, sodium acetate (10 mM) was used as the buffer, DMSO (2% v/v) was used as the non-aqueous solvent for the bortezomib premix and the primary tonicity adjustor, and mannitol (25 mg/mL) as a solubilizer and stabilizer. Osmolalities of select formulations (batch 67 and 82) were measured and were about 452-476 mOsmol/kg. Therefore, in addition to functioning as a solubilizer and stabilizer, mannitol also provides additional tonicity

TABLE 9

Bortezomib RTU Formulations at 2.5 mg/mL with Solubilizer/Stabilizer—Long Term Stability Testing at 2-8° C.

| Batch # (pH) | Time Point | Assay (%) | Imp. A | Imp. C | Imp. F | Chiral | Imp. D | Max. Single Unknown | Total |
|---|---|---|---|---|---|---|---|---|---|
| | 2.5 mg/mL bortezomib; 10 mM acetate, 2% (v/v) DMSO; 25 mg/mL mannitol |
| 74 (pH 4) | Initial | 100.1 | 0.01 | 0.01 | 0.02 | 0.01 | 0.02 | 0.04 | 0.11 |
|  | 3 M | 97.3 | 0.18 | 1.17 | 0.05 | 0.01 | 2.05 | 0.15 | 4.11 |
|  | 6 M | 99.3 | 0.48 | 2.35 | 0.10 | ND | 4.31 | 0.32 | 8.40 |
|  | 9 M | 85.1 | 0.94 | 4.21 | 0.22 | ND | 7.76 | 0.65 | 15.01 |
|  | 12 M | 95.4 | 0.65 | 1.81 | 0.13 | 0.01 | 3.36 | 0.25 | 6.79 |
|  | 15 M | 77.7 | 1.79 | 5.87 | 0.43 | ND | 11.03 | 0.72 | 22.01 |
|  | 23 M | 77.4 | 1.58 | 7.04 | 0.41 | ND | 11.72 | 0.87 | 23.60 |
| 82 (pH 4.5) | Initial | 95.0 | 0.01 | 0.03 | ND | 0.01 | 0.03 | 0.01 | 0.09 |
|  | 3 M | 98.4 | 0.09 | 0.06 | ND | ND | 0.10 | 0.02 | 0.29 |
|  | 6 M | 99.1 | 0.19 | 0.14 | 0.01 | 0.01 | 0.25 | 0.03 | 0.64 |
|  | 9 M | 97.2 | 0.23 | 0.14 | 0.01 | 0.01 | 0.25 | 0.03 | 0.71 |
|  | 12 M | 98.8 | 0.36 | 0.21 | 0.02 | 0.01 | 0.37 | 0.03 | 1.05 |
|  | 15 M | 98.9 | 0.46 | 0.27 | 0.03 | ND | 0.48 | 0.03 | 1.34 |
|  | 21 M | 94.6 | 0.64 | 0.84 | 0.05 | ND | 0.48 | 0.07 | 3.06 |
| 65 (pH 5) | Initial | 97.2 | 0.02 | 0.01 | 0.01 | 0.03 | 0.04 | 0.07 | 0.20 |
|  | 3 M | 99.2 | 0.16 | 0.21 | 0.03 | 0.03 | 0.30 | 0.08 | 0.84 |
|  | 5 M | 105.6 | 0.17 | 0.16 | 0.02 | ND | 0.25 | 0.07 | 0.69 |
|  | 6 M | 102 | 0.23 | 0.27 | 0.04 | 0.02 | 0.43 | 0.08 | 1.12 |
|  | 9 M | 94.1 | 0.29 | 0.25 | 0.04 | 0.03 | 0.43 | 0.08 | 1.18 |
|  | 12 M | 100.9 | 0.68 | 0.33 | 0.05 | 0.02 | 0.51 | 0.10 | 1.76 |
|  | 28 M | 99.6 | 0.51 | 0.45 | 0.07 | 0.06 | 0.69 | 0.07 | 1.85 |
| 83 (pH 5) | Initial | 95.4 | 0.01 | 0.05 | ND | ND | 0.03 | 0.01 | 0.10 |
|  | 3 M | 98.4 | 0.10 | 0.09 | ND | ND | 0.12 | 0.02 | 0.35 |
|  | 6 M | 95.6 | 0.18 | 0.12 | 0.01 | 0.01 | 0.19 | 0.03 | 0.56 |
|  | 9 M | 98.2 | 0.23 | 0.14 | 0.01 | 0.01 | 0.27 | 0.03 | 0.71 |
|  | 12 M | 98.1 | 0.34 | 0.26 | 0.02 | 0.01 | ND | 0.04 | 1.18 |
|  | 15 M | 98.4 | 0.44 | 0.26 | 0.02 | 0.01 | 0.43 | 0.04 | 1.24 |
|  | 22 M | 93.1 | 0.51 | 0.34 | <0.05 | <0.05 | 0.45 | <0.05 | 1.29 |
| 77 (pH 5.5) | Initial | 101.8 | 0.01 | 0.04 | 0.02 | 0.01 | 0.01 | 0.04 | 0.13 |
|  | 3 M | 103.8 | 0.12 | 0.06 | 0.02 | 0.03 | 0.06 | 0.08 | 0.42 |
|  | 5 M | 102.2 | 0.22 | 0.10 | 0.03 | 0.03 | 0.11 | 0.09 | 0.60 |
|  | 6 M | 99.6 | 0.33 | 0.22 | 0.04 | 0.05 | 0.26 | 0.09 | 1.02 |
|  | 9 M | 98.9 | 0.42 | 0.18 | 0.05 | 0.05 | 0.23 | 0.09 | 1.08 |
|  | 12 M | 98.5 | 0.46 | 0.16 | 0.04 | 0.02 | 0.21 | 0.08 | 1.02 |
|  | 23 M | 102.5 | 0.51 | 0.18 | 0.05 | 0.11 | 0.22 | 0.08 | 1.14 |
| 84 (pH 5.5) | Initial | 95.2 | 0.01 | 0.05 | ND | 0.01 | 0.02 | 0.01 | 0.09 |
|  | 3 M | 98.1 | 0.10 | 0.09 | 0.01 | ND | 0.08 | 0.02 | 0.30 |
|  | 6 M | 97.4 | 0.19 | 0.13 | 0.01 | 0.02 | 0.16 | 0.02 | 0.56 |
|  | 9 M | 97.8 | 0.23 | 0.19 | 0.02 | 0.02 | 0.26 | 0.03 | 0.78 |
|  | 12 M | 100.3 | 0.35 | 0.17 | 0.02 | 0.02 | ND | 0.03 | 0.86 |
|  | 15 M | 98.1 | 0.46 | 0.24 | 0.03 | 0.02 | 0.34 | 0.04 | 1.17 |
|  | 22 M | 95.7 | 0.54 | 0.26 | <0.05 | 0.07 | 0.30 | <0.05 | 1.16 |
| 812 (pH 5.5) | Initial | 95.9 | ND | 0.10 | ND | ND | 0.07 | <0.05 | 0.17 |
|  | 2 M | 97.7 | <0.05 | 0.12 | ND | ND | 0.11 | <0.05 | 0.23 |
|  | 3 M | 97.1 | 0.05 | 0.14 | <0.05 | ND | 0.12 | <0.05 | 0.31 |
|  | 6 M | 97.6 | 0.10 | 0.20 | <0.05 | ND | 0.16 | <0.05 | 0.46 |
|  | 9 M | 96.8 | 0.14 | 0.21 | <0.05 | ND | 0.20 | <0.05 | 0.55 |
|  | 12 M | 96.8 | 0.20 | 0.20 | <0.05 | 0.06 | 0.25 | <0.05 | 0.72 |
|  | 18 M | 94.5 | 0.35 | 0.40 | 0.05 | 0.06 | 0.37 | <0.05 | 1.22 |
|  | 24 M | 92.2 | 0.44 | 0.38 | 0.06 | 0.06 | 0.48 | <0.05 | 1.42 |
| 67 | Initial | 95.1 | 0.03 | 0.07 | 0.02 | 0.04 | 0.04 | 0.07 | 0.27 |

TABLE 9-continued

Bortezomib RTU Formulations at 2.5 mg/mL with Solubilizer/Stabilizer—Long Term Stability Testing at 2-8° C.

| Batch # (pH) | Time Point | Assay (%) | Imp. A | Imp. C | Imp. F | Chiral | Imp. D | Max. Single Unknown | Total |
|---|---|---|---|---|---|---|---|---|---|
| | 2.5 mg/mL bortezomib; 10 mM acetate, 2% (v/v) DMSO; 25 mg/mL mannitol |
| (pH 6) | 3 M | 110.9 | 0.20 | 0.11 | 0.04 | 0.06 | 0.05 | 0.08 | 0.55 |
|  | 5 M | 104.3 | 0.25 | 0.09 | 0.04 | 0.07 | 0.04 | 0.07 | 0.57 |
|  | 6 M | 97.0 | 0.31 | 0.13 | 0.05 | 0.12 | 0.06 | 0.08 | 0.76 |
|  | 9 M | 91.6 | 0.44 | 0.11 | 0.06 | 0.14 | 0.08 | 0.08 | 0.94 |
|  | 12 M | 96.9 | 1.00 | 0.18 | 0.09 | 0.18 | 0.11 | 0.09 | 1.71 |
|  | 28 M | 98.3 | 0.64 | 0.16 | 0.08 | 0.26 | 0.10 | 0.07 | 1.31 |
| 78 | Initial | 97.8 | 0.01 | 0.03 | 0.02 | 0.02 | 0.01 | 0.04 | 0.14 |
| (pH 6) | 3 M | 101.5 | 0.15 | 0.09 | 0.03 | 0.05 | 0.04 | 0.07 | 0.45 |
|  | 6 M | 98.7 | 0.27 | 0.13 | 0.04 | 0.06 | 0.08 | 0.08 | 0.71 |
|  | 9 M | 97.6 | 0.42 | 0.15 | 0.05 | 0.14 | 0.10 | 0.07 | 0.98 |
|  | 12 M | 97.7 | 0.51 | 0.17 | 0.07 | 0.12 | 0.13 | 0.08 | 1.15 |
|  | 15 M | 97.2 | 0.58 | 0.16 | 0.07 | 0.09 | 0.13 | 0.08 | 1.16 |
|  | 23 M | 98.6 | 0.65 | 0.22 | 0.09 | 0.24 | 0.17 | 0.07 | 1.45 |

ND = Not detected

As shown in Table 9, bortezomib ready-to-use formulations at 2.5 mg/mL, containing a non-aqueous solvent, a buffer, a solubilizer/stabilizer and a tonicity adjuster, is not sufficiently stable to storage at pH values below 4.5. Acceptable stability profiles are observed for pH values ranging from about 4.5 to 6 for these compositions.

The room temperature stability testing under room temperature conditions (25° C., 60% RH for at least 6 months) of these tonicity adjuster/stabilizer-containing formulations is presented in Table 10. The accelerated stability data corroborate the results of the long-term stability testing, with significant degradation observed at pH 4. At higher pH values, acceptable stability profiles are observed for at least 3 months of storage and in some formulations, even up to 6 months, particularly at pH 5.5. The accelerated data appear to show an optimal pH of between 5 and 6 for these formulations.

TABLE 10

Bortezomib RTU Formulations at 2.5 mg/mL with Stabilizer—Accelerated Stability Testing at 25° C.

| Batch # (pH) | Time Point | Assay (%) | Imp. A | Imp. C | Imp. F | Chiral | Imp. D | Max. Single Unknown | Total |
|---|---|---|---|---|---|---|---|---|---|
| | 2.5 mg/mL bortezomib; 10 mM acetate, 2% (v/v) DMSO; 25 mg/mL mannitol |
| 74 | Initial | 100.1 | 0.01 | 0.01 | 0.02 | 0.01 | 0.02 | 0.04 | 0.11 |
| (pH 4) | 1 M | 93.1 | 0.35 | 0.64 | 0.07 | 0.01 | 1.12 | 0.08 | 2.51 |
|  | 2 M | 93.0 | 0.87 | 2.88 | 0.31 | 0.01 | 5.27 | 0.48 | 10.76 |
|  | 3 M | 85.4 | 1.18 | 3.68 | 0.50 | 0.01 | 6.79 | 0.49 | 13.12 |
|  | 6 M | 65.7 | 2.80 | 8.30 | 2.08 | ND | 15.39 | 1.43 | 32.74 |
| 82 | Initial | 95.0 | 0.01 | 0.03 | ND | 0.01 | 0.03 | 0.01 | 0.09 |
| (pH 4.5) | 1 M | 98.1 | 0.25 | 0.07 | 0.01 | 0.01 | 0.13 | ND | 0.46 |
|  | 2 M | 92.6 | 0.48 | 0.10 | 0.02 | 0.01 | 0.19 | 0.02 | 0.83 |
|  | 3 M | 93.3 | 0.85 | 0.17 | 0.03 | 0.01 | 0.29 | 0.03 | 1.42 |
|  | 6 M | 92.3 | 1.53 | 0.42 | 0.11 | 0.02 | 0.77 | 0.04 | 2.98 |
| 65 | Initial | 97.2 | 0.02 | 0.01 | 0.01 | 0.03 | 0.04 | 0.07 | 0.20 |
| (pH 5) | 1 M | 97.5 | 0.32 | 0.10 | 0.03 | 0.06 | 0.16 | 0.08 | 0.82 |
|  | 2 M | 100.0 | 0.55 | 0.21 | 0.08 | 0.06 | 0.30 | 0.10 | 1.35 |
|  | 3 M | 105.8 | 1.09 | 0.26 | 0.13 | 0.11 | 0.44 | 0.15 | 2.29 |
|  | 6 M | 95.8 | 1.15 | 0.39 | 0.33 | 0.18 | 0.65 | 0.96 | 3.81 |
| 83 | Initial | 95.4 | 0.01 | 0.05 | ND | ND | 0.03 | 0.01 | 0.10 |
| (pH 5) | 1 M | 98.3 | 0.26 | 0.09 | 0.01 | 0.02 | 0.04 | 0.01 | 0.53 |
|  | 2 M | 94.6 | 0.50 | 0.12 | 0.02 | 0.02 | 0.21 | 0.02 | 0.91 |
|  | 3 M | 97.1 | 0.89 | 0.22 | 0.05 | 0.01 | 0.37 | 0.05 | 1.66 |
|  | 6 M | 94.8 | 1.56 | 0.29 | 0.11 | 0.05 | 0.52 | 0.05 | 2.66 |
| 77 | Initial | 101.8 | 0.01 | 0.04 | 0.02 | 0.01 | 0.01 | 0.04 | 0.13 |
| (pH 5.5) | 1 M | 99.2 | 0.38 | 0.09 | 0.04 | 0.08 | 0.09 | 0.08 | 0.77 |
|  | 2 M | 96.8 | 0.69 | 0.12 | 0.07 | 0.13 | 0.16 | 0.08 | 1.30 |
|  | 3 M | 101.8 | 0.97 | 0.13 | 0.10 | 0.15 | 0.20 | 0.08 | 1.70 |
|  | 6 M | 96.7 | 2.08 | 0.19 | 0.24 | 0.34 | 0.32 | 0.08 | 3.38 |

TABLE 10-continued

Bortezomib RTU Formulations at 2.5 mg/mL with Stabilizer—Accelerated Stability Testing at 25° C.

| Batch # (pH) | Time Point | Assay (%) | Imp. A | Imp. C | Imp. F | Chiral | Imp. D | Max. Single Unknown | Total |
|---|---|---|---|---|---|---|---|---|---|
| 2.5 mg/mL bortezomib; 10 mM acetate, 2% (v/v) DMSO; 25 mg/mL mannitol | | | | | | | | | |
| 84 | Initial | 95.2 | 0.01 | 0.05 | ND | 0.01 | 0.02 | 0.01 | 0.09 |
| (pH 5.5) | 1 M | 91.3 | 0.28 | 0.09 | 0.02 | 0.03 | 0.11 | 0.03 | 0.56 |
| | 2 M | 94.0 | 0.57 | 0.13 | 0.04 | 0.06 | 0.19 | 0.02 | 1.04 |
| | 3 M | 96.6 | 1.01 | 0.20 | 0.08 | 0.07 | 0.28 | 0.03 | 1.73 |
| | 6 M | 93.4 | 1.75 | 0.28 | 0.22 | 0.19 | 0.47 | 0.06 | 3.04 |
| 812 | Initial | 95.9 | ND | 0.10 | ND | ND | 0.07 | <0.05 | 0.17 |
| (pH 5.5) | 1 M | 96.2 | 0.34 | 0.12 | 0.05 | 0.10 | 0.14 | <0.05 | 0.75 |
| | 2 M | 95.6 | 0.62 | 0.14 | 0.08 | 0.16 | 0.19 | 0.05 | 1.24 |
| | 3 M | 96.4 | 0.91 | 0.17 | 0.12 | 0.22 | 0.23 | 0.06 | 1.70 |
| | 6 M | 93.1 | 1.71 | 0.26 | 0.27 | 0.35 | 0.34 | 0.09 | 3.01 |
| 67 | Initial | 95.1 | 0.03 | 0.07 | 0.02 | 0.04 | 0.04 | 0.07 | 0.27 |
| (pH 6) | 1 M | 95.6 | 0.53 | 0.09 | 0.07 | 0.29 | ND | 0.10 | 1.15 |
| | 2 M | 99.7 | 0.94 | 0.10 | 0.12 | 0.48 | 0.06 | 0.11 | 1.91 |
| | 3 M | 106.8 | 1.87 | 0.15 | 0.36 | 0.90 | 0.11 | 0.09 | 3.49 |
| | 6 M | 88.8 | 3.03 | 0.11 | 0.44 | 1.41 | 0.09 | 0.09 | 5.26 |
| 78 | Initial | 97.8 | 0.01 | 0.03 | 0.02 | 0.02 | 0.01 | 0.04 | 0.14 |
| (pH 6) | 1 M | 95.7 | 0.50 | 0.13 | 0.07 | 0.20 | 0.06 | 0.08 | 1.08 |
| | 2 M | 93.7 | 0.93 | 0.17 | 0.15 | 0.35 | 0.13 | 0.08 | 1.88 |
| | 3 M | 94.8 | 1.31 | 0.17 | 0.23 | 0.44 | 0.16 | 0.08 | 2.48 |
| | 6 M | 90.6 | 2.77 | 0.21 | 0.57 | 0.57 | 0.26 | 0.23 | 4.84 |

ND = Not detected

Example 10: Bortezomib Ready-to-Use Formulations in Phosphate Buffer

Exemplary formulations containing active ingredient (bortezomib), buffer, solubilizer and tonicity adjuster/stabilizer were prepared at various pH ranging from 6 to 7. In these formulations, sodium phosphate (10 mM) was used as the buffer, DMSO (2% v/v) was used as the non-aqueous solvent for the bortezomib premix and the primary tonicity adjustor, and mannitol (25 mg/mL) as a solubilizer and stabilizer. The long-term refrigerated stability testing under refrigerated conditions of such formulations is presented in Table 11 and the accelerated stability data in Table 12.

TABLE 11

Bortezomib RTU Formulations at 2.5 mg/mL with Phosphate Buffer—Long Term Stability Testing at 2-8° C.

| Batch # (pH) | Time Point | Assay (%) | Imp. A | Imp. C | Imp. F | Chiral | Imp. D | Max. Single Unknown | Total |
|---|---|---|---|---|---|---|---|---|---|
| 2.5 mg/mL bortezomib; 10 mM phosphate; 2% (v/v) DMSO; 25 mg/mL mannitol | | | | | | | | | |
| 79 | Initial | 92.2 | 0.01 | 0.04 | ND | 0.01 | 0.02 | 0.04 | 0.15 |
| (pH 6) | 3 M | 99.4 | 0.15 | 0.09 | 0.01 | 0.04 | 0.04 | 0.01 | 0.37 |
| | 6 M | 98.9 | 0.28 | 0.12 | 0.02 | 0.07 | 0.07 | 0.03 | 0.63 |
| | 9 M | 94.7 | 0.43 | 0.20 | 0.05 | 0.14 | 0.13 | 0.03 | 1.01 |
| | 12 M | 92.3 | 0.54 | 0.21 | 0.07 | 0.13 | 0.15 | 0.04 | 1.20 |
| | 15 M | 94.9 | 0.60 | 0.24 | 0.08 | 0.11 | 0.17 | 0.04 | 1.26 |
| | 23 M | 97.0 | 0.69 | 0.40 | 0.12 | 0.27 | 0.25 | ND | 1.72 |
| 80 | Initial | 92.2 | 0.01 | 0.04 | ND | 0.02 | ND | ND | 0.09 |
| (pH 6.5) | 3 M | 97.9 | 0.24 | 0.08 | 0.03 | 0.13 | 0.03 | 0.02 | 0.54 |
| | 6 M | 99.3 | 0.46 | 0.11 | 0.06 | 0.22 | 0.04 | 0.03 | 0.93 |
| | 9 M | 93.7 | 0.72 | 0.16 | 0.10 | 0.39 | 0.59 | 0.03 | 1.48 |
| | 12 M | 89.3 | 0.86 | 0.15 | 0.13 | 0.41 | 0.06 | 0.04 | 1.71 |
| | 15 M | 92.4 | 1.01 | 0.21 | 0.17 | 0.40 | 0.08 | 0.04 | 1.94 |
| | 23 M | 95.3 | 1.23 | 0.32 | 0.28 | 0.73 | 0.13 | ND | 2.69 |
| 81 | Initial | 94.2 | 0.02 | 0.03 | 0.01 | 0.02 | 0.02 | 0.02 | 0.12 |
| (pH 7) | 3 M | 96.2 | 0.41 | 0.06 | 0.07 | 0.20 | 0.02 | 0.01 | 0.77 |
| | 6 M | 94.9 | 0.76 | 0.07 | 0.13 | 0.48 | 0.02 | 0.02 | 1.49 |
| | 9 M | 92.2 | 1.18 | 0.11 | 0.20 | 0.85 | 0.02 | 0.02 | 2.39 |
| | 12 M | 91.3 | 1.45 | 0.09 | 0.28 | 0.74 | 0.03 | 0.02 | 2.63 |
| | 15 M | 95.0 | 1.66 | 0.13 | 0.33 | 0.92 | 0.04 | 0.01 | 3.10 |
| | 23 M | 94.5 | 1.50 | 0.16 | 0.33 | 1.06 | 0.05 | ND | 3.10 |

ND = Not detected

TABLE 12

Bortezomib RTU Formulations at 2.5 mg/mL with Phosphate
Buffer—Accelerated Stability Testing at 25° C.

| Batch # (pH) | Time Point | Assay (%) | Imp. A | Imp. C | Imp. F | Chiral | Imp. D | Max. Single Unknown | Total |
|---|---|---|---|---|---|---|---|---|---|
| 2.5 mg/mL bortezomib; 10 mM phosphate; 2% (v/v) DMSO; 25 mg/mL mannitol | | | | | | | | | |
| 79 (pH 6) | Initial | 92.2 | 0.01 | 0.04 | ND | 0.01 | 0.02 | 0.04 | 0.15 |
| | 1 M | 94.0 | 0.52 | 0.11 | 0.06 | 0.22 | 0.05 | 0.03 | 1.01 |
| | 2 M | 90.6 | 0.99 | 0.18 | 0.17 | 0.40 | 0.13 | 0.06 | 1.93 |
| | 3 M | 95.1 | 1.38 | 0.19 | 0.27 | 0.56 | 0.19 | 0.07 | 2.64 |
| | 6 M | 87.4 | 2.94 | 0.27 | 0.78 | 1.14 | 0.29 | 0.30 | 5.89 |
| 80 (pH 6.5) | Initial | 92.2 | 0.01 | 0.04 | ND | 0.02 | ND | ND | 0.09 |
| | 1 M | 91.0 | 0.96 | 0.12 | 0.17 | 0.65 | 0.03 | 0.04 | 1.98 |
| | 2 M | 87.1 | 1.75 | 0.17 | 0.37 | 1.13 | 0.06 | 0.05 | 3.53 |
| | 3 M | 86.5 | 2.47 | 0.14 | 0.56 | 1.52 | 0.06 | 0.05 | 4.81 |
| | 6 M | 76.7 | 5.14 | 0.23 | 1.72 | 3.06 | 0.13 | 0.07 | 10.44 |
| 81 (pH 7) | Initial | 94.2 | 0.02 | 0.03 | 0.01 | 0.02 | 0.02 | 0.02 | 0.12 |
| | 1 M | 89.0 | 1.62 | 0.08 | 0.34 | 1.34 | 0.01 | 0.02 | 3.43 |
| | 2 M | 83.1 | 2.89 | 0.11 | 0.70 | 2.32 | 0.03 | 0.02 | 6.10 |
| | 3 M | 84.5 | 4.09 | 0.10 | 1.18 | 2.93 | 0.04 | 0.02 | 8.38 |
| | 6 M | 66.8 | 8.27 | 0.12 | 3.10 | 5.90 | 0.06 | 0.76 | 18.39 |

ND = Not detected

The data presented in Table 11 demonstrate that acceptable stability of the 2.5 mg/mL bortezomib formulations in 10 mM phosphate buffer with 2% DMSO solubilizer and 25 mg/mL mannitol at pH values of 6 to 7 on long-term storage at 2-8° C. The phosphate buffered formulations at the higher pH range (compared to the acetate buffered formulations of Example 9) are less stable at the accelerated stability condition. Acceptable stability is observed for 3 months of accelerated stability at pH 6, but decreases with increasing pH (2 months at pH 6.5, and only 1 month at pH 7). The higher pH formulations thus are still acceptable for long-term refrigerated storage.

Example 11: Development of a Lyophilizer-Based Process for Controlling Headspace Oxygen Content The traditional process for controlling headspace oxygen (HSO) in a manufacturing process relies on flushing the headspace of the vials with sterile-filtered nitrogen immediately prior to stoppering and sealing the vial. However, robust process control with such a process is difficult to achieve; for example, there is often a lag between the nitrogen flush and the stoppering process that can result in variability in the HSO levels of the vials during the manufacturing process. Therefore, a process based on using a lyophilizer was developed to control the HSO levels in filled vials. In this process, vials are filled with the product, partially stoppered with lyo stoppers, and loaded into a lyophilizer. The product is then frozen briefly before evacuating the chamber to a target vacuum level; this evacuates the air in the headspace of each vial. Once the target vacuum level is reached (and before any drying of the product can occur), the vacuum is released by backfilling the lyophilizer with nitrogen. This process essentially replaces the air in the headspace of the vials with nitrogen. The steps of evacuation and back-filling may be repeated additional times if needed. The vials are then completely stoppered, the product is allowed to thaw, unloaded from the lyophilizer, and sealed. Because the process is carried out with all the filled vials in the lyophilizer at the same time, it minimizes any potential for vial-to-vial variability that may occur with the traditional process.

Two exemplary formulations, one at each bortezomib concentration, were prepared as per the general procedure in Example 6. After filling, the vials were partially stoppered with fluoropolymer-coated chlorobutyl rubber lyo stoppers and loaded into a laboratory scale lyophilizer. The freezing and evacuation of the headspace and backfilling with nitrogen, was performed as per process summarized in Table 13.

TABLE 13

Process for HSO Control for Laboratory-Scale Batches of Bortezomib Ready-to-use Formulations

| Step | Description |
|---|---|
| Freezing | Bring shelf temperature to −20° C., hold for 60 minutes. |
| Evacuation and backfill cycle #1 | Evacuate chamber to 150 millitorr. Hold for 0 minutes. Maintain shelf temperature at −20° C. during this step. Backfill chamber to 800 torr with Nitrogen. Hold for 5 minutes Maintain shelf temperature at −20° C. during this step. |
| Evacuation and backfill cycle #2 | Evacuate chamber to 150 millitorr. Hold for 0 minutes. Maintain shelf temperature at −20° C. during this step. Backfill chamber to 800 torr with Nitrogen. Hold for 5 minutes Maintain shelf temperature at −20° C. during this step. |
| Evacuation and backfill cycle #3 | Evacuate chamber to 150 millitorr. Hold for 0 minutes. Maintain shelf temperature at −20° C. during this step. Backfill chamber to 800 torr with Nitrogen. Hold for 5 minutes Maintain shelf temperature at −20° C. during this step. |
| Final evacuation and backfill cycle | Evacuate chamber to 150 millitorr. Hold for 0 minutes. Maintain shelf temperature at −20° C. during this step. Backfill chamber to 76 torr with Nitrogen. Hold for 0 minutes. Completely seat stoppers in lyo chamber by collapsing shelves. Maintain shelf temperature at −20° C. during this step. |
| Thawing | Raise shelf temperature to +20° C. |
| Unloading | Complete stoppering, break vacuum and unload |

The batches prepared in this manner were placed on long-term (2-8C) and accelerated stability (25° C.), and the results are reported in Table 14 and 15, respectively.

TABLE 14

Bortezomib RTU Formulations with Lyophilizer Based Process for HSO Control—Long Term Stability Testing at 2-8° C.

| Batch # (pH) | Time Point | Assay (%) | Imp. A | Imp. C | Imp. F | Chiral | Imp. D | Max Single Unknown | Total |
|---|---|---|---|---|---|---|---|---|---|
| 2.5 mg/mL bortezomib; 25 mg/mL mannitol; 10 mM acetate; 2% (w/v) DMSO ||||||||||
| 17-810 (pH 5.5) | Initial | 99.4 | ND | 0.10 | ND | ND | 0.08 | <0.05 | 0.18 |
| | 2 M | 99.4 | <0.05 | 0.13 | ND | ND | 0.11 | <0.05 | 0.24 |
| | 3 M | 96.6 | 0.05 | 0.14 | <0.05 | ND | 0.12 | <0.05 | 0.31 |
| | 6 M | 97.3 | 0.09 | 0.42 | <0.05 | ND | 0.33 | <0.05 | 0.83 |
| | 9 M | 100.1 | 0.14 | 0.25 | <0.05 | ND | 0.23 | <0.05 | 0.61 |
| | 12 M | 98.2 | 0.20 | 0.21 | <0.05 | 0.07 | 0.26 | <0.05 | 0.74 |
| | 18 M | 95.0 | 0.35 | 0.45 | 0.05 | 0.06 | 0.39 | <0.05 | 1.28 |
| 1 mg/mL bortezomib; 25 mg/mL mannitol; 10 mM acetate; 2% (v/v) DMSO ||||||||||
| 17-811 (pH 6) | Initial | 101.6 | ND | 0.11 | ND | <0.05 | 0.08 | <0.05 | 0.19 |
| | 2 M | 103.0 | 0.05 | 0.14 | <0.05 | <0.05 | 0.10 | <0.05 | 0.29 |
| | 3 M | 102.5 | 0.07 | 0.14 | <0.05 | <0.05 | 0.09 | <0.05 | 0.39 |
| | 6 M | 102.8 | 0.12 | 0.18 | <0.05 | 0.05 | 0.12 | <0.05 | 0.47 |
| | 9 M | 103.4 | 0.18 | 0.20 | <0.05 | 0.05 | 0.13 | <0.05 | 0.56 |
| | 12 M | 99.5 | 0.25 | 0.16 | <0.05 | 0.11 | 0.15 | <0.05 | 0.67 |
| | 18 M | 99.6 | 0.43 | 0.32 | 0.07 | 0.13 | 0.20 | <0.05 | 1.15 |
| | 24 M | 97.2 | 0.56 | 0.24 | 0.09 | 0.15 | 0.23 | <0.05 | 1.26 |

ND = Not Detected

TABLE 15

Bortezomib RTU Formulations with Lyophilizer Based Process for HSO Control—Accelerated Stability Testing at 25° C.

| Batch # (pH) | Time Point | Assay (%) | Imp. A | Imp. C | Imp. F | Chiral | Imp. D | Max Single Unknown | Total |
|---|---|---|---|---|---|---|---|---|---|
| 2.5 mg/mL bortezomib; 25 mg/mL mannitol; 10 mM acetate; 2% DMSO ||||||||||
| 17-810 (pH 5.5) | Initial | 99.4 | ND | 0.10 | ND | ND | 0.08 | <0.05 | 0.18 |
| | 1 M | 100.7 | 0.37 | 0.13 | 0.05 | 0.11 | 0.16 | <0.05 | 0.83 |
| | 2 M | 94.1 | 0.61 | 0.16 | 0.09 | 0.16 | 0.21 | 0.05 | 1.28 |
| | 3 M | 94.7 | 0.95 | 0.19 | 0.14 | 0.23 | 0.24 | 0.06 | 1.81 |
| | 6 M | 95.3 | 1.77 | 0.36 | 0.30 | 0.39 | 0.36 | 0.09 | 3.17 |
| 1 mg/mL bortezomib; 25 mg/mL mannitol; 10 mM acetate; 2% DMSO ||||||||||
| 17-811 (pH 6) | Initial | 101.6 | ND | 0.11 | ND | <0.05 | 0.08 | <0.05 | 0.19 |
| | 1 M | 100.9 | 0.48 | 0.15 | 0.10 | 0.25 | 0.11 | <0.05 | 1.08 |
| | 2 M | 98.7 | 0.83 | 0.13 | 0.16 | 0.39 | 0.12 | 0.06 | 1.74 |
| | 3 M | 98.6 | 1.21 | 0.16 | 0.23 | 0.54 | 0.14 | 0.09 | 2.44 |
| | 6 M | 95.7 | 2.37 | 0.20 | 0.45 | 0.95 | 0.17 | 0.19 | 4.41 |

ND = Not Detected

Example 12: Bortezomib RTU Formulation Batches at Manufacturing Scale

Two scale-up demonstration batches (10 L) were manufactured, one each with formulations at the 1 mg/mL and 2.5 mg/mL. These batches served to confirm elements and steps of the manufacturing process:

- Pre-dissolving the batch quantity of the bortezomib drug substance in the batch quantity of dimethyl sulfoxide (premix)
- Dissolution of batch quantities of sodium acetate and mannitol in 50% of the batch volume of Water for Injection and adjusting the pH of the initial bulk solution with sodium hydroxide or hydrochloric acid
- Addition of bortezomib/dimethyl sulfoxide premix to the aqueous mannitol/acetate solution.
- Making up the batch volume to 90% of the target volume with Water for Injection and final pH adjustment if needed.
- Final batch volume makeup to the target batch volume with Water for Injection.
- Sterile filtering into glass vials, partially stoppering with lyo stoppers, and using the lyophilizer to control the HSO of the vials.
- Complete stoppering, sealing, and 100% testing of the vials for HSO as well as visual inspection.

Additionally, a simplified process using the lyophilizer was developed for the HSO control with a single evacuation and backfilling cycle as summarized in Table 16.

TABLE 16

Modified Process for HSO Control for Pilot-Scale Batches of Bortezomib Ready-to-use Formulations

| Step | Description |
|---|---|
| Freezing | Bring shelf temperature to −45° C. over 120 minutes, hold for 60 minutes. |
| Evacuation and backfill | Evacuate chamber to 0.2 millibar. Hold for 2 minutes. Maintain shelf temperature at −45° C. during this step. Backfill chamber to 975 millibar bar with Nitrogen. |
| cycle #1 | Maintain shelf temperature at −45° C. during this step. |
| Thawing | Bring shelf temperature to +4° C., hold for 60 minutes. |
| Unloading | Complete stoppering, break vacuum and unload |

The batches prepared in this manner were placed on long-term (2-8C) and accelerated stability (25° C.), and the results are reported in Table 17 and 18, respectively.

TABLE 17

Pilot-Scale Batches of Bortezomib RTU Formulations—Long Term Stability Testing at 2-8° C.

| Batch # (pH) | Time Point | Assay (%) | Imp. A | Imp. C | Imp. F | Chiral | Imp. D | Max Single Unknown | Total |
|---|---|---|---|---|---|---|---|---|---|
| \multicolumn{10}{c}{2.5 mg/mL bortezomib; 25 mg/mL mannitol; 10 mM acetate; 2% (v/v) DMSO} | | | | | | | | | |
| BORCD1019(D) (pH 5.5) | Initial | 98.7 | BLD | 0.14 | BLD | BLQ | BLQ | BLD | 0.14 |
|  | 2 M | 97.3 | 0.08 | 0.11 | BLD | BLQ | 0.07 | BLQ | 0.27 |
|  | 3 M | 97.8 | 0.1 | 0.1 | BLD | 0.1 | 0.1 | BLQ | 0.4 |
|  | 6 M | 97.6 | 0.2 | 0.2 | BLQ | 0.1 | 0.1 | BLQ | 0.5 |
|  | 9 M | 97.6 | 0.2 | 0.2 | BLQ | 0.1 | 0.1 | BLQ | 0.5 |
|  | 12 M | 97.8 | 0.3 | 0.1 | BLQ | 0.1 | 0.1 | BLQ | 0.5 |
|  | 18 M | 97.4 | 0.4 | 0.1 | BLQ | 0.1 | 0.2 | 0.1 | 0.7 |
|  | 24 M | 97.6 | 0.5 | 0.1 | BLQ | 0.1 | 0.2 | BLQ | 0.9 |
| \multicolumn{10}{c}{1 mg/mL bortezomib; 25 mg/mL mannitol; 10 mM acetate; 2% (w/v) DMSO} | | | | | | | | | |
| BORDD1019(D) (pH 5.75) | Initial | 98.4 | BLD | 0.13 | BLD | 0.05 | BLQ | BLQ | 98.4 |
|  | 2 M | 99.4 | 0.08 | 0.14 | BLQ | 0.05 | 0.08 | BLQ | 99.4 |
|  | 3 M | 98.3 | 0.2 | 0.2 | BLQ | 0.1 | 0.1 | BLQ | 98.3 |
|  | 6 M | 99.9 | 0.2 | 0.1 | BLQ | 0.1 | 0.1 | BLQ | 99.9 |
|  | 9 M | 100.0 | 0.3 | 0.2 | BLQ | 0.1 | 0.2 | 0.1 | 100.0 |
|  | 12 M | 100.9 | 0.4 | 0.2 | BLQ | 0.1 | 0.2 | 0.1 | 100.9 |
|  | 18 M | 98.2 | 0.6 | 0.2 | 0.1 | 0.1 | 0.2 | BLQ | 98.2 |
|  | 24 M | 98.4 | BLD | 0.13 | BLD | 0.05 | BLQ | BLQ | 98.4 |

BLD = below 0.017% limit of detection;
BLQ = below 0.05% limit of quantitation

TABLE 18

Pilot-Scale Batches of Bortezomib RTU Formulations—Accelerated Stability Testing at 25° C.

| Batch # (pH) | Time Point | Assay (%) | Imp. A | Imp. C | Imp. F | Chiral | Imp. D | Max Single Unknown | Total |
|---|---|---|---|---|---|---|---|---|---|
| \multicolumn{10}{c}{2.5 mg/mL bortezomib; 25 mg/mL mannitol; 10 mM acetate; 2% (v/v) DMSO} | | | | | | | | | |
| BORCD1019(D) (pH 5.5) | Initial | 98.7 | BLD | 0.14 | BLD | BLQ | BLQ | BLD | 0.14 |
|  | 1 M | 98.3 | 0.35 | 0.12 | BLQ | 0.11 | 0.08 | BLQ | 0.68 |
|  | 2 M | 97.2 | 0.67 | 0.19 | 0.06 | 0.17 | 0.11 | BLQ | 1.23 |
|  | 3 M | 95.7 | 0.98 | 0.09 | 0.08 | 0.23 | 0.11 | BLQ | 1.51 |
|  | 6 M | 94.9 | 1.9 | 0.1 | 0.2 | 0.4 | 0.1 | 0.1 | 2.9 |
| \multicolumn{10}{c}{1 mg/mL bortezomib; 25 mg/mL mannitol; 10 mM acetate; 2% (w/v) DMSO} | | | | | | | | | |
| BORDD1019(D) (pH 5.75) | Initial | 98.4 | BLD | 0.13 | BLD | 0.05 | BLQ | BLQ | 0.18 |
|  | 1 M | 99.1 | 0.35 | 0.22 | 0.05 | 0.12 | 0.10 | BLQ | 0.87 |
|  | 2 M | 97.0 | 0.70 | 0.10 | 0.09 | 0.20 | 0.11 | BLQ | 1.21 |
|  | 3 M | 96.5 | 1.02 | 0.09 | 0.12 | 0.27 | 0.13 | BLQ | 1.65 |
|  | 6 M | 94.4 | 2.0 | 0.1 | 0.3 | 0.5 | 0.2 | 0.2 | 3.2 |

BLD = below 0.017% limit of detection;
BLQ = below 0.05% limit of quantitation

Example 13: Effect of Oxygen Headspace on the Long-Term Storage Stability (2-8° C.) of Bortezomib Formulations Because bortezomib is known to be oxidation sensitive, the effect of oxygen level in the headspace of the filled vials on the stability of the formulations was assessed. The bortezomib formulation at 1 mg/mL was used for this study as the lower concentration is considered a worst-case in terms of stability. The formulation was prepared as per the general procedure outlined in Example 12. After filling and sealing, vials were tested for headspace oxygen (HSO) content using a laser-based non-destructive test. Vials were segregated into three groups based on the HSO level: Group A wherein the HSO levels were about 1.5%-2.5% oxygen (Formulation 1019(D)A); Group B with about 2.5%-3.5% oxygen (Formulation 1019(D)B); and Group C with about 3.5%-5.1% oxygen (Formulation 1019(D)C). The long-term stability of these formulations when stored at 2-8° C. was assessed by measuring the Assay and the impurities of bortezomib using HPLC method and is summarized in Table 19.

mg/mL mannitol adjusted to pH 5.5 (using sodium hydroxide or hydrochloric acid) or 1 mg/mL bortezomib in 10 mM acetate buffer with 2% (w/v) DMSO solubilizer and 10 mg/mL mannitol adjusted to pH 5.75 (using sodium hydroxide or hydrochloric acid). The hemolytic potential of Bortezomib RTU Injection (1 mg/mL and 2.5 mg/mL) in human whole blood was compared to the reference product VELCADE (bortezomib) for Injection. Three aliquots of human blood (single donor) were incubated at 37° C. (±5° C.) for 30 to 35 minutes with Bortezomib RTU formulations or VELCADE at either 1 mg/mL or 2.5 mg/mL strengths at a final drug concentration of 5000 ng/mL in blood. This final drug concentration tested is more than 20-fold higher than the reported $C_{max}$ (223 ng/mL) reported for VELCADE after repeat intravenous administration. After incubation, the study samples were centrifuged and the supernatant was tested for hemoglobin content. The percent hemolysis of each sample was calculated based on the hemoglobin content of the supernatant, expressed as a percentage of hemoglobin content of the donor sample, after correcting for dilution and interference from the sample, if any. A percent hemolysis value of >25% is considered to be definitive as

TABLE 19

Effect of HSO Level on the Long-Term Stability (2-8° C.)

| | | | Impurities (%) | | | | | |
|---|---|---|---|---|---|---|---|---|
| HSO Level (% O₂ v/v) | Time Point | Assay | Imp. A | Imp. C | Imp. F | Chiral | Imp. D | Max Single Unknown | Total |

1 mg/mL bortezomib; 10 mg/mL mannitol 10 mM acetate; 2 (w/v) % DMSO

| HSO Level (% O₂ v/v) | Time Point | Assay | Imp. A | Imp. C | Imp. F | Chiral | Imp. D | Max Single Unknown | Total |
|---|---|---|---|---|---|---|---|---|---|
| 1019(D)A | Initial | 98.4 | BLD | 0.13 | BLD | 0.05 | BLQ | BLQ | 0.18 |
| (1.5-2.5%) | 4 M | 99.1 | 0.10 | 0.19 | BLQ | BLQ | 0.13 | BLQ | 0.43 |
| | 6 M | 97.4 | 0.15 | 0.16 | BLQ | 0.05 | 0.14 | BLQ | 0.49 |
| | 12 M | 100.2 | 0.24 | 0.28 | BLQ | 0.05 | 0.27 | BLQ | 0.84 |
| | 18 M | 99.9 | 0.37 | 0.19 | BLQ | 0.11 | 0.24 | BLQ | 0.91 |
| | 24 M | 99.5 | 0.45 | 0.19 | 0.06 | 0.09 | 0.30 | BLQ | 1.09 |
| 1019(D)B | Initial | 98.4 | BLD | 0.13 | BLD | 0.05 | BLQ | BLQ | 0.18 |
| (2.5-3.5%) | 4 M | 99.3 | 0.10 | 0.25 | BLQ | BLQ | 0.17 | BLQ | 0.52 |
| | 6 M | 98.2 | 0.14 | 0.18 | BLQ | 0.05 | 0.15 | BLQ | 0.52 |
| | 12 M | 99.5 | 0.24 | 0.27 | BLQ | 0.05 | 0.25 | BLQ | 0.80 |
| | 18 M | 99.7 | 0.36 | 0.23 | 0.05 | 0.11 | 0.30 | BLQ | 1.05 |
| | 24 M | 99.2 | 0.43 | 0.27 | 0.07 | 0.09 | 0.40 | BLQ | 1.26 |
| 1019(D)C | Initial | 98.4 | BLD | 0.13 | BLD | 0.05 | BLQ | BLQ | 0.18 |
| (3.5-5.1%) | 4 M | 100.3 | 0.10 | 0.28 | BLQ | 0.05 | 0.18 | BLQ | 0.57 |
| | 6 M | 96.8 | 0.14 | 0.19 | BLQ | 0.05 | 0.15 | BLQ | 0.53 |
| | 12 M | 99.7 | 0.24 | 0.27 | BLQ | 0.05 | 0.25 | BLQ | 0.80 |
| | 18 M | 99.3 | 0.34 | 0.24 | 0.05 | 0.10 | 0.28 | BLQ | 1.00 |
| | 24 M | 99.7 | 0.44 | 0.24 | 0.06 | 0.09 | 0.35 | BLQ | 1.19 |

BLD = below 0.017% limit of detection;
BLQ = below 0.05% limit of quantitation

Remarkably, stability results provided in Table 18 indicate that there is no influence of HSO level within the range tested (i.e., between about 1.5% to 5.1% by volume) and that the assay and the impurity profile of the three HSO conditions are comparable. This result was surprising because bortezomib is susceptible to oxidation in presence of molecular oxygen and it was expected that a higher HSO level would have significantly higher impurities when compared to those with lower HSO levels.

Example 14: Hemolytic Potential of Bortezomib Ready-to-Use Formulations Compared to VELCADE A GLP-compliant in vitro hemolysis study was conducted to establish the safety of Bortezomib RTU formulations. The formulations consisted of 2.5 mg/mL bortezomib in 10 mM acetate buffer with 2% (v/v) DMSO solubilizer and 25 positive for hemolysis, while a percent hemolysis value of <10% is considered to be definitive as negative for hemolysis.

TABLE 20

In Vitro Hemolytic Potential of Bortezomib Ready-to-Use Formulations Compared to VELCADE

| Treatment [Final bortezomib concentration in blood] | Hemoglobin (mg/dL) of Supernatant Average ± Standard Deviation [Range] | % Hemolysis[†] Average ± Standard Deviation [Range] |
|---|---|---|
| Bortezomib RTU Injection, 1 mg/mL [5000 ng/mL] | 11.7 ± 3.2 [Range: 8-14] | 0.18 ± 0.05 [Range: 0.13-0.22] |

TABLE 20-continued

In Vitro Hemolytic Potential of Bortezomib Ready-to-Use Formulations Compared to VELCADE

| Treatment [Final bortezomib concentration in blood] | Hemoglobin (mg/dL) of Supernatant Average ± Standard Deviation [Range] | % Hemolysis[†] Average ± Standard Deviation [Range] |
|---|---|---|
| VELCADE, 1 mg/mL [5000 ng/mL] | 11.0 ± 2.0 [Range: 9-13] | 0.17 ± 0.03 [Range: 0.14-0.17] |
| Bortezomib RTU Injection, 2.5 mg/mL [5000 ng/mL] | 11.0 ± 0.0 [Range: All 11] | 0.17 ± 0.00 [Range: All 0.17] |
| VELCADE, 2.5 mg/mL [5000 ng/mL] | 9.7 ± 1.5 [Range: 8-11] | 0.15 ± 0.02 [Range: 0.13-0.17] |
| 0.9% Saline-Negative Control | 9.3 ± 3.0 [Range: 9-10] | 0.15 ± 0.01 [Range: 0.14-0.16] |
| 1% Saponin-Positive Control | 6359 ± 235.5 [Range: 6287-6428] | 99.36 ± 1.1 [Range: 98.23-100.44] |

[†] = Calculated using a dilution factor of 2 and Hb content of donor of 12,800 mg/dL.

Example 15: Comparison of Pharmacodynamic Activity of Bortezomib Ready-to-Use 1 mg/mL Formulations and VELCADE in an In Vitro Assay Bortezomib is a proteasome inhibitor. Therefore, the inhibitory potential of bortezomib ready-to-use formulations and VELCADE on the activity of human proteasomes was determined in a definitive in vitro pharmacodynamic proteasome inhibition assay. The bortezomib formulation at 1 mg/mL comprising 10 mM sodium acetate, 10 mg/mL mannitol, 2% (w/v) DMSO, pH adjusted to 5.75 with hydrochloric acid or sodium hydroxide was used for this study. The study was performed using the 1 mg/mL strength. Proteasome inhibition by bortezomib RTU Injection and, separately, VELCADE (bortezomib) for Injection (after reconstitution in 0.9% sodium chloride to 1 mg/mL) was determined at 8 concentrations of bortezomib (nominal concentrations of 7.81, 15.63, 31.25, 62.5, 125, 250, 500 and 1000 ng/mL) in 96-well microtiter plates using a commercially available proteasome inhibition kit. The extent of inhibition of proteasome activity is reported in terms of % remaining activity at each concentration for both the bortezomib RTU formulation and VELCADE in Table 21 based on 27 measurements (three replicates on nine plates).

TABLE 21

Summary of Proteasome Inhibition Results by Bortezomib RTU 1 mg/mL Formulation and VELCADE for Injection

| Bortezomib Nominal Concentration in Spiking Solution (ng/mL) | Average Percent Remaining Activity ± Standard Deviation (% RSD) | |
|---|---|---|
| | Bortezomib RTU 1 mg/mL | VELCADE 1 mg/mL |
| 7.81 | 96.9 ± 9.6 (9.9) | 99.9 ± 7.5 (7.5) |
| 15.63 | 87.9 ± 7.5 (8.6) | 88.2 ± 5.6 (6.3) |
| 31.25 | 76.3 ± 7.3 (9.6) | 77.6 ± 6.4 (8.3) |
| 62.5 | 64.0 ± 7.8 (12.2) | 66.2 ± 13.2 (20.0) |
| 125 | 42.0 ± 8.1 (19.9) | 37.9 ± 9.1 (24.0) |
| 250 | 20.1 ± 6.6 (33.4) | 18.4 ± 4.5 (24.1) |
| 500 | 8.4 ± 1.6 (18.5) | 8.1 ± 1.3 (16.2) |
| 1000 | 4.7 ± 0.8 (16.7) | 4.8 ± 0.7 (13.7) |

Overall, the proteasome activity decreased with increasing concentrations of both Test article and Reference article, indicating that both inhibited proteasome activity in a concentration dependent manner. The extent of inhibition is very similar for Bortezomib RTU Injection 1 mg/mL and VELCADE (bortezomib) for Injection under the conditions of the study.

The similarity or equivalence of the in vitro proteasome inhibitory activity of two formulations of bortezomib was evaluated using the methodology and recommendations in USP <1032> Design and Development of Biological Assays and USP <1034> Analysis of Biological Assays. A four-parameter-logistic (4-PL) function (equation 3.5 of USP <1034>) was used for regression analyses. Because the response curves are nonlinear, an evaluation of the chi-square criteria for testing curve parallelism was performed in accordance with the USP recommendations. Equivalence was then determined in terms of relative potency by computing the ratio of the inflexion point ($EC_{50}$) of the Test over the Reference Drug, consistent with USP <1034> (section 3.4 Nonlinear Models for Quantitative Responses). Additionally, the Two-One-sided 95% confidence intervals (or equivalently the 90% confidence intervals) of the Relative Potency were also determined.

The similarity between the Bortezomib RTU formulation and VELCADE is confirmed by the parallelism analyses as the computed chi-square statistic fell within the 95% % upper tail cut-off of a chi-squared distribution. The Relative Potency (of bortezomib RTU formulation compared to VELCADE) is determined to be 103.4%, with the 90% confidence intervals ranging from 99.3% to 107.5%. These are well within the 80% to 125% limits for bioequivalence typically used by FDA. Thus, the bortezomib ready-to-use formulations disclosed herein are equivalent in terms of in vitro pharmacodynamic activity compared to VELCADE.

Example 16: Comparison of Pharmacodynamic Activity of Bortezomib Ready-to-Use 2.5 Mg/mL Formulations and VELCADE in an In Vitro Assay The definitive in vitro pharmacodynamic proteasome inhibition assay of Example 15 was performed with bortezomib formulation at 2.5 mg/mL comprising 10 mM sodium acetate, 25 mg/mL mannitol, 2.2% (w/v) DMSO, pH adjusted to 5.5 with hydrochloric acid or sodium hydroxide. The extent of inhibition of proteasome activity is reported in terms of % remaining activity at each concentration for both the bortezomib RTU formulation and VELCADE in Table 22 based on 27 measurements (three replicates on nine plates).

TABLE 22

Summary of Proteasome Inhibition Results by Bortezomib RTU 2.5 mg/mL Formulation and VELCADE for Injection

| Bortezomib Nominal Concentration in Spiking Solution (ng/mL) | Average Percent Remaining Activity ± Standard Deviation (%RSD) | |
|---|---|---|
| | Bortezomib RTU 2.5 mg/mL | VELCADE 2.5 mg/mL |
| 7.81 | 92.2 ± 5.21 (5.65) | 90.2 ± 7.62 (8.45) |
| 15.63 | 77.1 ± 5.22 (6.77) | 76.7 ± 7.33 (9.56) |
| 31.25 | 57.2 ± 5.19 (9.07) | 58.0 ± 7.17 (12.4) |
| 62.5 | 37.0 ± 5.35 (14.5) | 35.0 ± 6.05 (17.3) |

TABLE 22-continued

Summary of Proteasome Inhibition Results by Bortezomib RTU
2.5 mg/mL Formulation and VELCADE for Injection

| Bortezomib Nominal Concentration in Spiking Solution (ng/mL) | Average Percent Remaining Activity ± Standard Deviation (%RSD) | |
| --- | --- | --- |
| | Bortezomib RTU 2.5 mg/mL | VELCADE 2.5 mg/mL |
| 125 | 19.3 ± 3.39 (17.6) | 18.5 ± 3.22 (17.4) |
| 250 | 10.4 ± 1.41 (13.6) | 10.6 ± 1.48 (13.9) |
| 500 | 6.54 ± 0.714 (10.9) | 6.71 ± 0.734 (10.9) |
| 1000 | 4.77 ± 0.421 (8.83) | 4.75 ± 0.370 (7.79) |

Overall, the proteasome activity decreased with increasing concentrations of both Test article and Reference article, indicating that both inhibited proteasome activity in a concentration dependent manner. The extent of inhibition is very similar for Bortezomib RTU Injection 2.5 mg/mL and VELCADE (bortezomib) for Injection under the conditions of the study.

Thus, the bortezomib ready-to-use formulations disclosed herein are equivalent in terms of in vitro pharmacodynamic activity compared to VELCADE.

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. In addition to the embodiments described herein, the present disclosure contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed is:

1. A method for administering bortezomib to a patient in need thereof comprising parenterally administering to the patient a liquid, ready-to-use aqueous composition consisting of about 1 mg/mL bortezomib, about 10 mg/mL mannitol, about 20 mg/mL dimethyl sulfoxide, about 0.82 mg/mL sodium acetate, water and, optionally, hydrochloric acid, sodium hydroxide, or a combination thereof, wherein the pH of the ready-to-use composition is about 5 to about 6.

2. The method of claim 1, wherein the composition has a pH of about 5.5 to about 6.

3. The method of claim 1, further comprising, prior to administration, filling the liquid composition in a vial, freezing the liquid composition in the vial, evacuating the head space in the vial, filling the head space with nitrogen, stoppering the vial, and thawing the vial.

4. The method of claim 1, wherein the patient suffers from cancer.

5. The method of claim 1, wherein the patient suffers from multiple myeloma.

6. The method of claim 1, wherein the patient suffers from mantle cell lymphoma.

7. A method for administering bortezomib to a patient in need thereof comprising parenterally administering to the patient a liquid, ready-to-use aqueous composition consisting of about 2.5 mg/mL bortezomib, about 25 mg/mL mannitol, about 22 mg/mL dimethyl sulfoxide, about 0.82 mg/mL sodium acetate, water and, optionally, hydrochloric acid, sodium hydroxide, or a combination thereof, wherein the pH of the ready-to-use composition is about 5 to about 6.

8. The method of claim 7, wherein the composition has a pH of about 5.25 to about 5.75.

9. The method of claim 7, further comprising, prior to administration, filling the liquid composition in a vial, freezing the liquid composition in the vial, evacuating the head space in the vial, filling the head space with nitrogen, stoppering the vial, and thawing the vial.

10. The method of claim 7, wherein the patient suffers from cancer.

11. The method of claim 7, wherein the patient suffers from multiple myeloma.

12. The method of claim 7, wherein the patient suffers from mantle cell lymphoma.

* * * * *